(12) United States Patent
Basile et al.

(10) Patent No.: US 10,543,317 B2
(45) Date of Patent: Jan. 28, 2020

(54) PREFILLED DISPOSABLE INJECTION DEVICE

(71) Applicants: Merck Sharp & Dohme Corp., Rahway, NJ (US); Peter A. Basile, Bloomsbury, NJ (US); Steven Carl Persak, Basking Ridge, NJ (US); Mikhail Gotliboym, Scotch Plains, NJ (US)

(72) Inventors: Peter A. Basile, Bloomsbury, NJ (US); Steven Carl Persak, Basking Ridge, NJ (US); Mikhail Gotliboym, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 101 days.

(21) Appl. No.: 15/312,845

(22) PCT Filed: Jun. 1, 2015

(86) PCT No.: PCT/US2015/033450
§ 371 (c)(1),
(2) Date: Nov. 21, 2016

(87) PCT Pub. No.: WO2015/187518
PCT Pub. Date: Dec. 10, 2015

(65) Prior Publication Data
US 2017/0197031 A1  Jul. 13, 2017

Related U.S. Application Data

(60) Provisional application No. 62/007,428, filed on Jun. 4, 2014.

(51) Int. Cl.
*A61M 5/24* (2006.01)
*A61M 5/28* (2006.01)
(Continued)

(52) U.S. Cl.
CPC .......... *A61M 5/2425* (2013.01); *A61M 5/282* (2013.01); *A61M 5/3129* (2013.01);
(Continued)

(58) Field of Classification Search
CPC .......... F16F 1/32; F16F 1/322; A61M 5/1454; A61M 5/2422; A61M 5/2425;
(Continued)

(56) References Cited

U.S. PATENT DOCUMENTS 2,950,717 A * 8/1960 Bonet ............... A61J 1/062
604/214
3,340,869 A * 9/1967 Bane ............... A61M 3/00
206/364
(Continued)

OTHER PUBLICATIONS

International Search Report for PCT/US2015/033450 dated Aug. 31, 2015, 9 pages.

*Primary Examiner* — Lauren P Farrar
*Assistant Examiner* — James D Ponton
(74) *Attorney, Agent, or Firm* — Janet E. Fair; Catherine D. Fitch

(57) ABSTRACT

The present invention relates to a drug delivery device comprising a drug container having at least one bellow. The at least one bellow has a first surface and an opposing second surface. The first surface is comprised of a first Belleville spring and the opposing second surface is comprised of a second Belleville spring, wherein the second Belleville spring has a higher spring rate than the first Belleville spring.

12 Claims, 27 Drawing Sheets

(51) Int. Cl.
*A61M 5/31* (2006.01)
*A61M 5/50* (2006.01)
*A61M 5/32* (2006.01)

(52) U.S. Cl.
CPC ........ *A61M 5/3137* (2013.01); *A61M 5/3216* (2013.01); *A61M 5/502* (2013.01); *A61M 2005/312* (2013.01)

(58) Field of Classification Search
CPC ........ A61M 5/281; A61M 5/282; A61M 5/50; A61M 5/5013; A61M 5/502; A61M 2205/273; A61M 2205/276
See application file for complete search history.

(56) References Cited

U.S. PATENT DOCUMENTS

| | | | |
|---|---|---|---|
| 3,473,524 A * | 10/1969 | Drewe | A61M 3/00 222/215 |
| 3,938,514 A | 2/1976 | Boucher | |
| 4,543,093 A * | 9/1985 | Christinger | A61M 5/31513 604/228 |
| 5,407,431 A * | 4/1995 | Botich | A61M 5/3129 604/110 |
| 5,693,021 A | 12/1997 | Diaz et al. | |
| 6,319,235 B1 | 11/2001 | Yoshino | |
| 6,916,305 B2 | 7/2005 | Jones et al. | |
| 2003/0167041 A1* | 9/2003 | Rosoff | A61M 5/282 604/232 |
| 2007/0191780 A1* | 8/2007 | Modi | A61M 5/282 604/187 |
| 2009/0076450 A1* | 3/2009 | Caizza | A61M 5/502 604/110 |
| 2011/0218499 A1* | 9/2011 | Cahen | A61M 5/2425 604/216 |
| 2012/0220948 A1* | 8/2012 | Barbour | A61M 5/3137 604/189 |
| 2013/0281940 A1 | 10/2013 | Gelblum et al. | |

* cited by examiner

PREFILLED DISPOSABLE INJECTION DEVICE

CROSS-REFERENCE TO RELATED APPLICATIONS

This application is a U.S. National Phase application under 35 U.S.C. § 371 of PCT Application No. PCT/US2015/033450, filed Jun. 1, 2015, which published as WO2015/187518A1 on Dec. 10, 2015, and claims priority under 35 U.S.C. § 365(b) from U.S. provisional patent application No. 62/007,428, filed Jun. 4, 2014.

FIELD OF THE INVENTION

The present invention relates generally to drug delivery devices. Specifically, the invention is directed to an injection device that incorporates a drug container that cannot be refilled post use, preventing possible re-use of the drug delivery device.

BACKGROUND

In many cases, it is not only the cost of a drug that prohibits a treatment from becoming widely accessible but also the cost of packaging. Many companies strive to reduce the cost of proven life-saving treatments so that such treatments can be more readily accessible.

Reducing the cost of traditional packaging is one example of a way to lower the cost of such treatments. Reducing the cost of traditional packaging of pre-filled syringes has been an area of focus for some time. The problem with traditional packaging of pre-filled syringes is two-fold. The first is the cost of the primary glass drug container. The second is the cost of filling the glass container. Manufacturing and filling, are by their very nature, two distinct processes. The first step is to form the container and then one must pack it up and ship it. Then the container must be unpacked at the container filling facility and then filled.

An additional problem that plagues conventional syringes is that conventional syringes can be refilled and reused. Re-using syringes contributes to the transmission of blood borne diseases like HIV. Thus, there is a need for a low-cost syringe that cannot be refilled or reused.

SUMMARY

The drug delivery device described herein provides a solution to the problems of traditional syringes discussed above.

For the purpose of clarity, orientation references are hereby established for the description of this invention. The term "proximal" refers to a position that is close to the body of the person injecting a drug into the patient with the device. The term "distal" refers to a position that is away from the body of the person injecting the drug into the patient with the device.

Described herein are low-cost, pre-filled disposable syringes that cannot be refilled or re-used post use. The drug delivery device described herein includes a pre-filled drug container that remains locked in its post-use state. This feature ensures that all of the drug is dispensed from the drug container and the drug delivery device cannot be refilled or re-used post use. The drug delivery device described herein further provides a solution to the problems of traditional syringes discussed above as it is made of plastic that is pre-filled during the container's manufacturing process eliminating the use of costly glass containers that need to be shipped and filled.

Described herein is a drug delivery device comprising a drug container comprising at least one bellow, wherein the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring.

Also, described herein is a drug delivery device comprising a drug container comprising at least one bellow, wherein the at least one bellow comprises a first surface and an opposing second surface, wherein the first surface is comprised of a first Belleville spring and the opposing second surface is comprised of a second Belleville spring, wherein the second Belleville spring is oriented opposite to the first Belleville spring, wherein the first and second Belleville spring are joined at their common outer edge, and wherein the second Belleville spring has a higher spring rate than the first Belleville spring.

In certain embodiments, the drug container of the drug delivery devices described herein comprises one bellow. In certain embodiments, the drug container of the drug delivery devices described herein comprises a series of axially aligned bellows. The number of axially-aligned bellows of the drug container of the delivery device described herein is limited only by internal volume requirements and by the requirement for the drug container to resist buckling under an axial compressive load. In certain embodiments, the drug container of the drug delivery devices described herein comprises a series of two axially aligned bellows. In certain embodiments, the drug container of the drug delivery devices described herein comprises a series of two or more axially aligned bellows. In certain embodiments, the drug container of the drug delivery devices described herein comprises a series of three axially aligned bellows. In certain embodiments, the drug container of the drug delivery devices described herein comprises a series of three or more axially aligned bellows. In certain embodiments, the drug container of the drug delivery devices described herein comprises a series of four axially aligned bellows. In certain embodiments, the drug container of the drug delivery devices described herein comprises a series of four or more axially aligned bellows.

In certain embodiments, the drug container of the drug delivery devices described herein comprises a series of five axially aligned bellows. In certain embodiments, the drug container of the drug delivery devices described herein comprises a series of five or more axially aligned bellows. In certain embodiments, the drug container of the drug delivery devices described herein comprises a series of six axially aligned bellows. In certain embodiments, the drug container of the drug delivery devices described herein comprises a series of six or more axially aligned bellows. In certain embodiments, the drug container of the drug delivery devices described herein comprises a series of seven axially aligned bellows. In certain embodiments, the drug container of the drug delivery devices described herein comprises a series of seven or more axially aligned bellows. In certain embodiments, the drug container of the drug delivery devices described herein comprises a series of eight axially aligned bellows. In certain embodiments, the drug container of the drug delivery devices described herein comprises a series of eight or more axially aligned bellows.

In certain embodiments, of the drug delivery device described herein, at least one of the bellows is stable in both the expanded state and in the compressed states.

The drug container of the drug delivery device described herein has a distal end and a proximal end. In certain embodiments, the arrangement of bellows in a drug container comprising more than one bellow comprises orientation of all of the first Belleville springs in the proximal direction, and orientation of all of the second Belleville springs in the distal direction. Orientation of all of the first Belleville springs in the same direction and all of the second Belleville springs in the opposite direction to the first Belleville springs allows the drug container to compress to its minimum volume with the lowest applied force.

In another embodiment, the arrangement of bellows in a drug container comprising of more than one bellow comprises orientation of all of the first Belleville springs in the distal direction, and orientation of all of the second Belleville springs in the proximal direction. In certain embodiments, comprising two or more bellows, the second Belleville springs may be situated adjacent to one another, whereby some of the first Belleville springs move in the proximal direction to abut their adjoining second Belleville springs, and whereby some of the first Belleville springs move in the distal direction to abut their adjoining second Belleville springs In certain embodiments of the drug delivery device described herein, wherein the drug container has one bellow, the drug container further comprises a top at the proximal end of the drug container, wherein the top encloses the proximal end of the drug container, and wherein the top is axially aligned with the bellow. In certain embodiments of the drug delivery device described herein, wherein the drug container has one bellow, the drug container further comprises an outlet port at the distal end, wherein the outlet port at the distal end of the drug container is axially aligned with the bellow. In alternate embodiments of the drug delivery device described herein, the outlet port at the distal end of the drug container is not axially aligned with the bellow.

In certain embodiments of the drug delivery devices described herein, wherein the drug container has a series of axially aligned bellows, the drug container further comprises a top at the proximal end of the drug container, wherein the top encloses the proximal end of the drug container, and wherein the top is axially aligned with the series of bellows. Certain embodiments of the drug container of the drug delivery devices described herein further comprise an outlet port at the distal end of the drug container, wherein the outlet port is axially aligned with the series of bellows. In alternate embodiments of the drug delivery device described herein, the outlet port at the distal end of the drug container is not axially aligned with the series of bellows.

In certain embodiments of the drug delivery device described herein, the drug delivery device further comprises a housing to accommodate the drug container. The housing has a distal end and a proximal end. In certain embodiments, the housing comprises at least one flange. In certain embodiments of the drug delivery device described herein, the housing comprises a pair of flanges. In certain embodiments, the housing comprises one or more flanges, wherein the flanges are displaced, from the distal end of the housing, a distance that allows the user's fingers to be held between the distal surface of the flanges and the patient's skin to stabilize the device during use. In certain embodiments, the housing comprises one or more flanges for secure placement of the user's fingers while the device is being used. In certain embodiments, the flanges may be fully closed. In certain embodiments, the flanges may be partially closed. In certain embodiments, said flanges may be hinged, wherein they can be rotated in the distal direction after the device is used and is removed from the patient, wherein, in such a rotated position the flanges enclose and protect the needle for safe disposal.

In certain embodiments, at the distal end of the drug container, the drug container comprises an integrally molded frangible seal. In other embodiments, at the distal end of the drug container, the drug container comprises a twist-off tab, wherein when the tab is removed, a needle has access to mating geometry on the drug container and can be attached to such geometry. In another embodiment, the distal end of the drug container can have a film or foil seal which can be removed to expose an opening on the drug container's distal end.

In another embodiment, the distal end of the drug container can be pierced by an extension of the needle in the proximal direction, so that the needle pierces the distal end of the drug container when it is secured to the device in a subsequent step. In another embodiment, the distal end of the drug container is manually pierced or cut off by the user prior to use. In alternate embodiments, the drug delivery device described herein further comprises a needle in communication with the outlet port of the drug container.

In certain embodiments, the drug container of the drug delivery devices described herein contains a drug product. In a preferred embodiment, the drug container is pre-filled with the drug product. In certain embodiments, the drug product is selected from the group consisting of oxytocin and carbetocin.

Also described herein is a drug delivery device comprising a drug container comprising a top and at least one bellow axially aligned with the top, wherein the at least one bellow comprises a first surface and an opposing second surface, wherein the first surface is comprised of a first Belleville spring and the second opposing surface is comprised of a second, opposing Belleville spring, wherein the second Belleville spring has a higher spring rate than the first Belleville spring, and an outlet port at the distal end of the drug container, wherein the outlet port at the distal end of the drug container is axially aligned with the at least one bellow; a housing, wherein the housing extends between distal and proximal ends, wherein the proximal end is open to receive the drug container, wherein the distal end is open to receive the distal end of the drug container; and a drug product contained within the drug container.

In alternate embodiments of the drug delivery device described herein, the outlet port at the distal end of the drug container is not axially aligned with any bellows.

In certain embodiments, the drug delivery device described herein has a pre-injection position or first position and a post-injection position or second position. In the first position, the drug container is extended axially to its full length, wherein the at least one bellow is expanded, wherein the volume contained within the drug container is maximized. In the second position, the drug container is compressed axially to its minimum length, wherein the at least one bellow is compressed, wherein the volume contained within the drug container is minimized.

With regard to the drug delivery devices described herein, there is no feature on the proximal end of the drug container to which a tensile force can be applied, whereby the drug container can be expanded from the second position back to the first position. In certain embodiments when the drug delivery devices described herein are in the second position, the drug delivery device has dispensed the drug product. In this position the delivery device cannot be refilled or reused.

In certain embodiments, the top of the drug container extends beyond the proximal end of the housing when the drug container is in its second position, whereby access to the top of the drug container is ensured. In an alternate embodiment, the top of the drug container is recessed slightly into the proximal end of the housing when the drug container is in its second position, but whereby access for the application of force to the top of the drug container can still occur. In certain embodiments when the drug containers described herein are in the second position the drug delivery device has dispensed the drug product. In this position the delivery device cannot be refilled or reused.

In certain embodiments the drug delivery device described herein further comprises a housing and a plunger, wherein the distal end of the plunger is in contact with the top of the drug container, and wherein the proximal end of the plunger extends out of the proximal end of the housing, whereby applying a force in the distal direction to the proximal end of the plunger compresses the drug container. In certain embodiments, the plunger comprises a means wherein the plunger cannot move in the proximal direction within the housing once the plunger has fully compressed the drug container. In a certain embodiments, the proximal end of the plunger extends beyond the proximal end of the housing for the entire range of movement of the drug container. In other embodiments, the housing comprises one or more flanges, whereby the flanges interact with the user's fingers for stabilizing the device during use. In certain embodiments, the plunger comprises a retention feature that interacts with the housing to prevent it from being removed from the housing at its maximum extension in the proximal direction. In these embodiments, the housing and plunger are configured to generally replicate the appearance and function of a pre-filled syringe.

In certain embodiments, the housing comprises an axial length that is a small fraction of the length of the drug container in its second, or compressed, position. In certain embodiments, the housing comprises one or more features that interact with mating features of the drug container to retain the distal end of the drug container in the housing.

In certain embodiments, less than 100% of the internal volume of the drug container is filled with the drug to be dispensed. The remaining fraction of the volume may be filled with air or another fluid that is not part of the therapy. This fraction must be expelled from the device before the device is used to dispense the drug to the patient, in an activity called priming. To enable priming, a means for partially compressing the drug container may be employed. In certain embodiments, wherein the drug container comprises two or more bellows, a fraction of those bellows can be designed to change state from the first position to the second position before the remaining bellows change state when the drug container is compressed. The priming bellows would comprise geometry that would cause them to change state under a lower applied force than the remaining bellows. The size and number of priming bellows would be selected so that the change in volume of these bellows, as they move from the first position to the second position, would be greater than the maximum volume to be expelled during priming. In a certain embodiments, one or more priming bellows are configured to be bistable, whereby they do not expand after being compressed Also described herein are methods of manufacturing the drug containers and the drug delivery devices described herein. In certain embodiments, the drug container is made using blow-fill-seal technology. In another embodiment, the drug container is made using form-fill-seal technology.

BRIEF DESCRIPTION OF THE FIGURES

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DESCRIPTION

Figure 1:
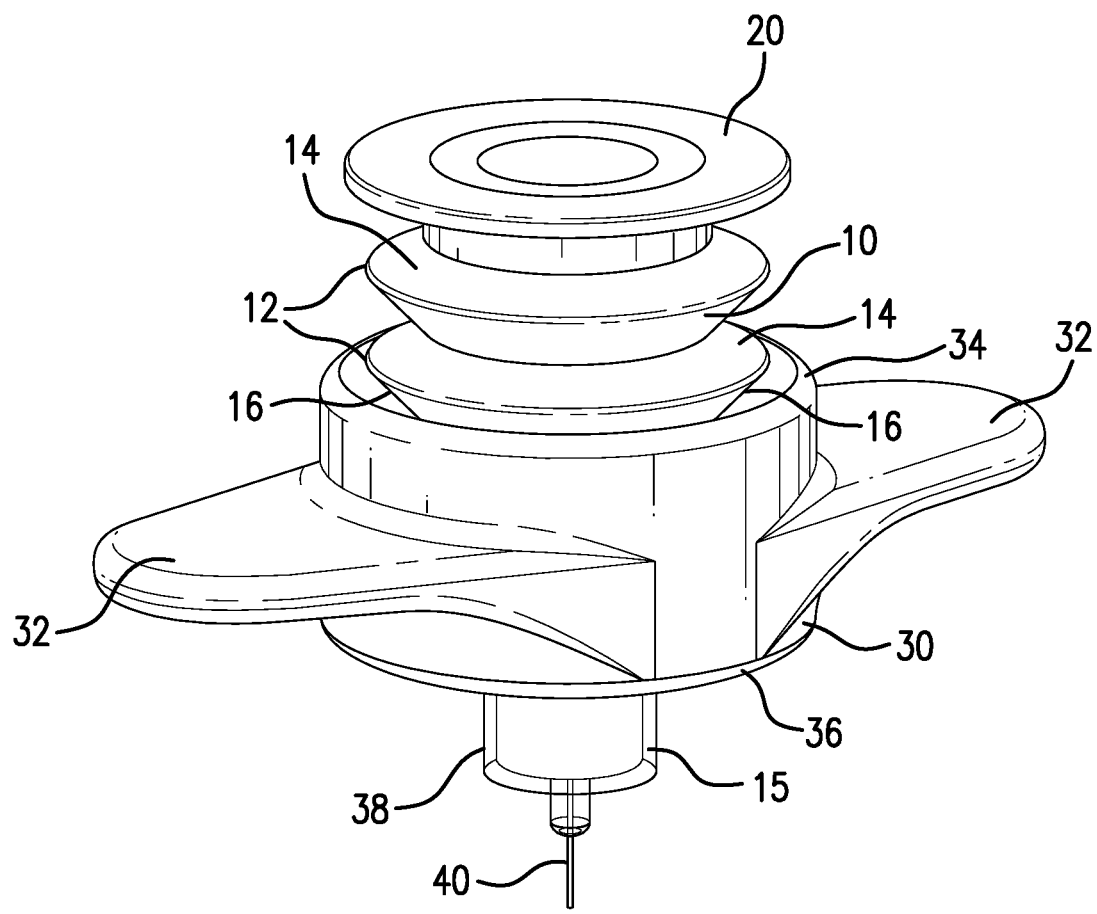
FIG. 1 is an embodiment of the drug delivery device described herein, in its pre-injection position or first position.

The following terms and phrases used herein are defined as follows unless otherwise noted:

"Bellow" means a flexible structure whose volume can be changed by compression or expansion.

With regard to the bellows contained in the drug delivery device described herein, when an axial tensile force is applied to a bellow, the Belleville springs are pulled apart. In this position, the bellow is expanded and the volume contained within the bellow is maximized.

When an axial compressive force is applied to the bellow, the Belleville springs are forced together such that their opposing internal surfaces abut each other. The first Belleville spring is softer and is proportioned such that when it is compressed, it passes through the neutral position into a second stable position where it abuts the second Belleville spring. The second stable position is a mirror image of the first, expanded position. Due to the relative spring rates and selected geometries, when an axial compressive load is applied to this set of Belleville springs, the second, stiffer, spring remains relatively static and the first, softer, spring deflects. When it is fully deflected into the second position, the bellow is compressed and volume contained within the bellow is minimized "Belleville spring" means a type of spring shaped like a washer that is three dimensional, wherein the inner diameter resides in a plane which is above the outer diameter's plane i.e. a frusto-conical shape, which gives the washer a spring characteristic. Belleville spring, disc spring, Belleville washer, conical compression washer, are all names for the same type of spring.

"Spring rate" or spring constant, is the relationship between the degree of deflection of a spring and the spring force generated in response to this deflection.

One of the key features of the drug delivery device described herein is that it contains a drug container that is comprised of at least one bellow with unique geometry comprising two opposing Belleville springs. This unique geometry prevents the drug container from restoring itself to its original or post-injection state once the drug product loaded into the container has been dispensed. This precludes the possibility of the drug delivery device from being refilled or re-used. This unique geometry also allows the drug container to have minimum residual volume when collapsed post-use, allowing the drug loaded into the drug container to be completely dispensed leaving no residual, wasted drug product in the container.

The drug delivery device described herein includes a drug container comprising at least one bellow that has a first surface and a second surface. The surfaces are formed by two opposing Belleville springs, a first Belleville spring forming the first surface and a second Belleville spring forming the second surface. The second Belleville spring is stiffer and has a higher spring rate then the first Belleville spring. The first Belleville spring is softer and is proportioned such that when it is compressed into the flat state, it snaps through the flat position into a second stable position. This second stable position is a mirror image of the initial, unstressed position. Due to the relative spring rates and selected geometries, when an axial load is applied to this set of Belleville springs, the second and stiffer spring remains relatively static, the first, softer spring begins to deflect. When it is deflected into its flat position it snaps through this position and becomes inverted.

This behavior produces two distinct benefits. First, as the first Belleville spring is now inverted and is nesting inside of the stiffer second Belleville spring, the residual volume of the bellow is a small fraction of the initial volume of the bellow when the bellow was in its original or starting position. Second, since the inverted state of the first Belleville spring is also stable, there is no restoring force. Because of this, there is no concern for "suck back" of the delivered drug product. Additionally, since there is no restoring force, the device cannot be refilled and reused.

By way of contrast, with conventional bellows the convolutions are mirror images, identical on either side of the fold or corrugation. Although conventional bellows can compress when an axial load is applied, the residual volume is substantial, and the bellows will recover to its initial geometry when the axial load is released. If conventional bellows were to be used in conjunction with a drug container for a drug delivery device, the substantial residual volume could contribute to a costly amount of unused drug product left in the device. Additionally, as conventional bellows return to its uncompressed state there is a risk of creating a vacuum which can lead to "suck-back" of drug product and under dosing. Also, because conventional bellows can easily return to their uncompressed state and create a vacuum, there is a possibility that the drug delivery device can be refilled and reused which can contribute to the spread of infectious diseases.

Referring to the figures, wherein like reference numerals designate like elements throughout the drawings, FIG. 1 shows an embodiment of the drug delivery device described herein, in its pre-injection position or first position. The embodiment of the drug delivery device shown in FIG. 1 has a drug container 10 comprising bellows, wherein bellows 12 have a first surface 14 and a second surface 16. First surface 14 is in the shape of a first Belleville spring and second surface 16 is in the shape of a second Belleville spring. The drug delivery device shown in FIG. 1 has a distal end and a proximal end. As shown in FIG. 1, drug container 10 has a top 20 located at the distal end of drug container 10 and an outlet port 15 located at the proximal end of drug container 10. Top 20 is axially aligned with bellows 12. Outlet port 15 is axially aligned with bellows 12. The drug delivery device shown in FIG. 1 also has a housing 30. The housing 30 extends between a proximal end 34 and a distal end 36, wherein the proximal end 34 is open to receive the drug container. Distal end 36 includes an outlet port column 38. The outlet port column 38 is capable of receiving the outlet port 15 of the drug container. The housing 30 also has a pair of flanges 32. The embodiment of the drug delivery device shown in FIG. 1 also has a needle 40 in communication with the outlet port 15 of the drug container 10.

Figure 2:
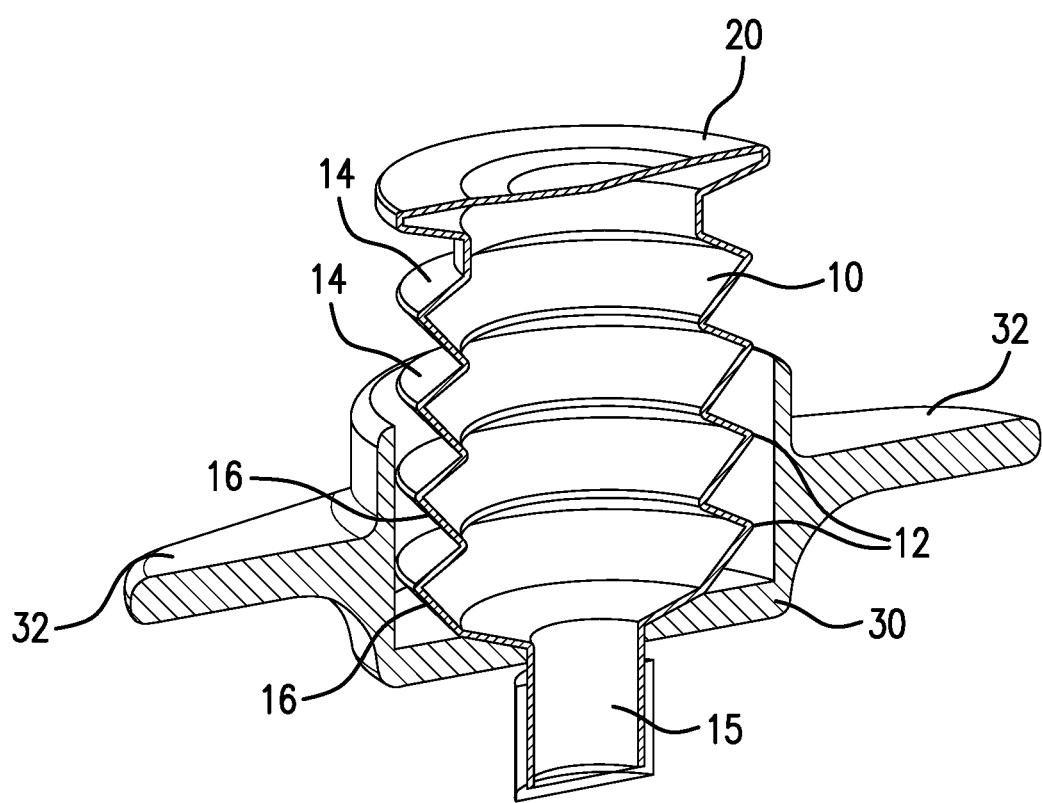
FIG. 2 is a cross-sectional view of an embodiment of the drug delivery device described herein, in its pre-injection position or first position.

FIG. 2 shows a cross-sectional view of an embodiment of the drug delivery device described herein, in its pre-injection position or first position. The embodiment of the drug delivery device shown in FIG. 2 has a drug container 10 comprising bellows 12, wherein the bellows have a first surface 14 and a second surface 16. The first surface 14 is in the shape of a first Belleville spring and the second surface 16 is in the shape of a second Belleville spring. As shown in the embodiment of FIG. 2, the drug container of the drug delivery device has a series of axially aligned bellows, specifically four axially aligned bellows. However, in other embodiments of the drug delivery device described herein, the drug container can have any number of bellows. In certain embodiments of the drug delivery device described herein, the drug container can have up to twenty, up to fifteen or up to twelve, axially aligned bellows. In certain embodiments of the drug delivery device described herein, the drug container can have two, three, five, six, seven, eight, nine, ten, eleven or twelve axially aligned bellows.

In the embodiment of the drug delivery device shown in FIG. 2, the drug container also has a top 20 and outlet port 15. As shown in FIG. 2 is housing 30 with flanges 32.

Figure 3:
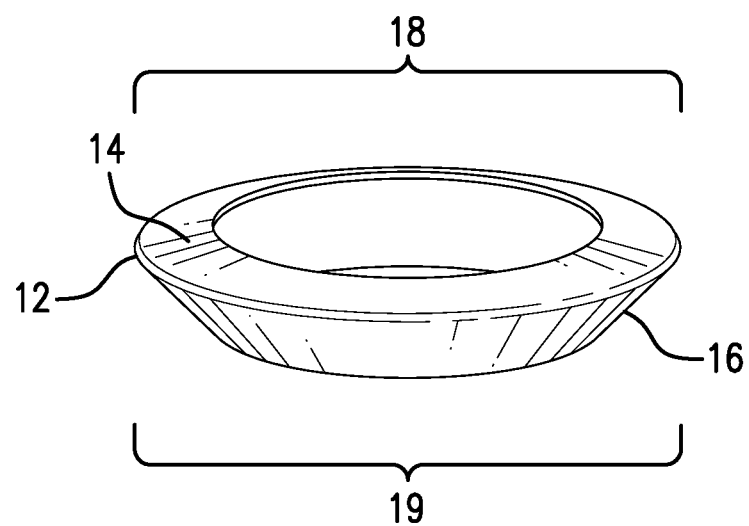
FIG. 3 is a perspective view of a bellow of an embodiment of the drug delivery device described herein, in its pre-injection position or first position.

FIG. 3 shows a perspective view of a bellow of an embodiment of a drug container of the delivery device described herein, in its pre-injection position or first position. FIG. 3 shows a bellow 12, wherein the bellow has a first surface 14 and a second surface 16. The first surface 14 is in the shape of a first Belleville spring 18 and the second surface 16 is in the shape of a second Belleville spring 19. The second Belleville spring 19 remains stationary when an axially compressive force is applied to the bellow. The first Belleville spring 18 is capable of deflecting and folding onto the second Belleville spring 19 when an axially compressive force is applied to the bellow.

Figure 4:
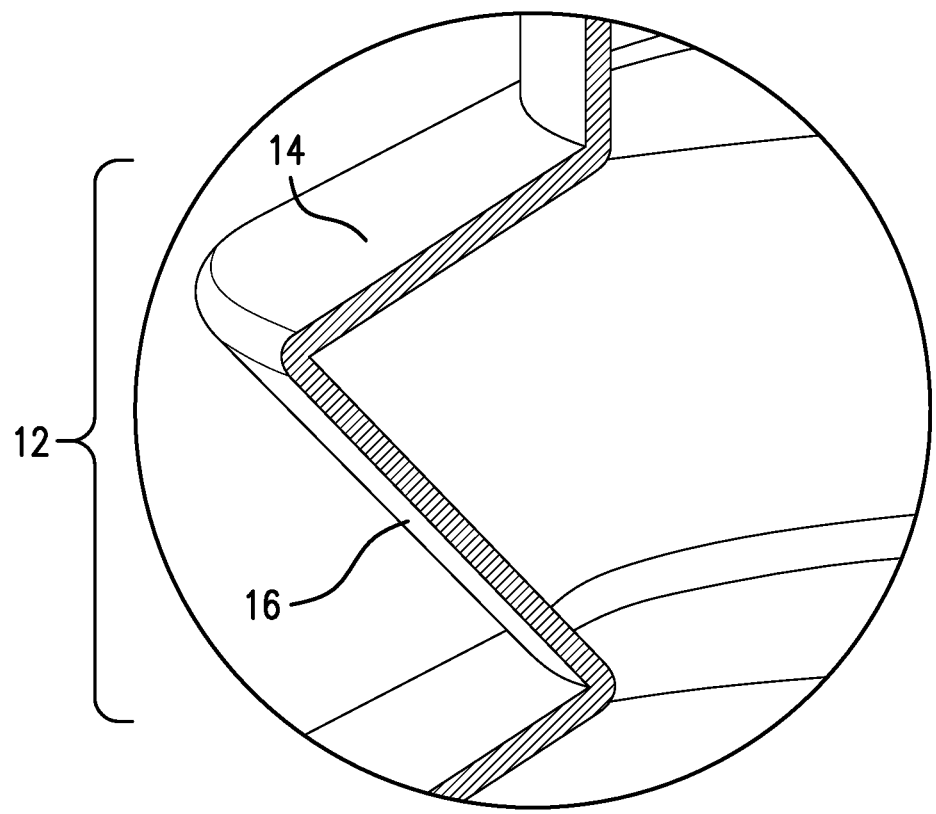
FIG. 4 is a partial, cross-sectional view of a bellow of an embodiment of the drug delivery device described herein, in its pre-injection position or first position.

FIG. 4 shows a partial cross-sectional view of a bellow of an embodiment of the drug delivery device described herein, in its pre-injection position or first position. FIG. 4 shows a bellow 12, wherein the bellow has a first surface 14 and a second surface 16.

Figure 5:
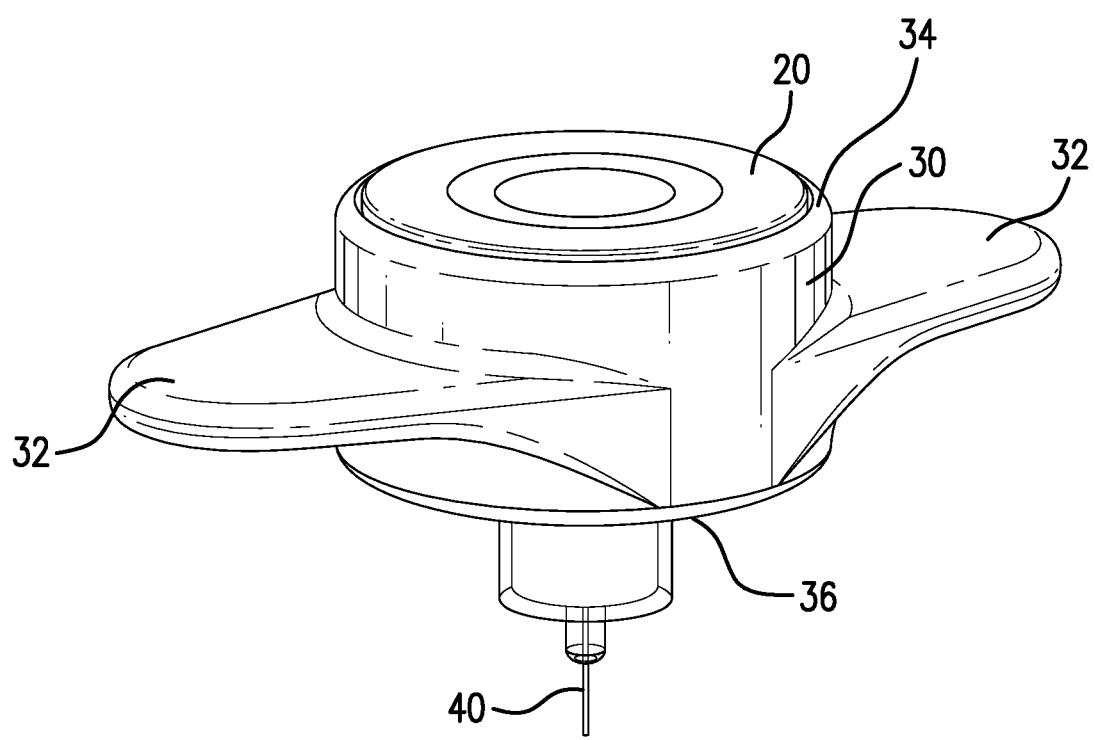
FIG. 5 is an embodiment of the drug delivery device described herein, in its post-injection position or second position.

FIG. 5 shows an embodiment of the drug delivery device described herein, in its post-injection position or second position. The embodiment of the drug delivery device shown in FIG. 5 shows the drug container top 20 and housing 30. The housing 30 extends between a proximal end 34 and a distal end 36, wherein the proximal end 34 is open to receive the drug container (not shown). When the drug delivery device described herein is in the post-injection or second position the drug container top 20 is substantially flush with the housing 30. The housing 30 has a pair of flanges 32. The embodiment of the drug delivery device shown in FIG. 5 also has a needle 40.

Figure 6:
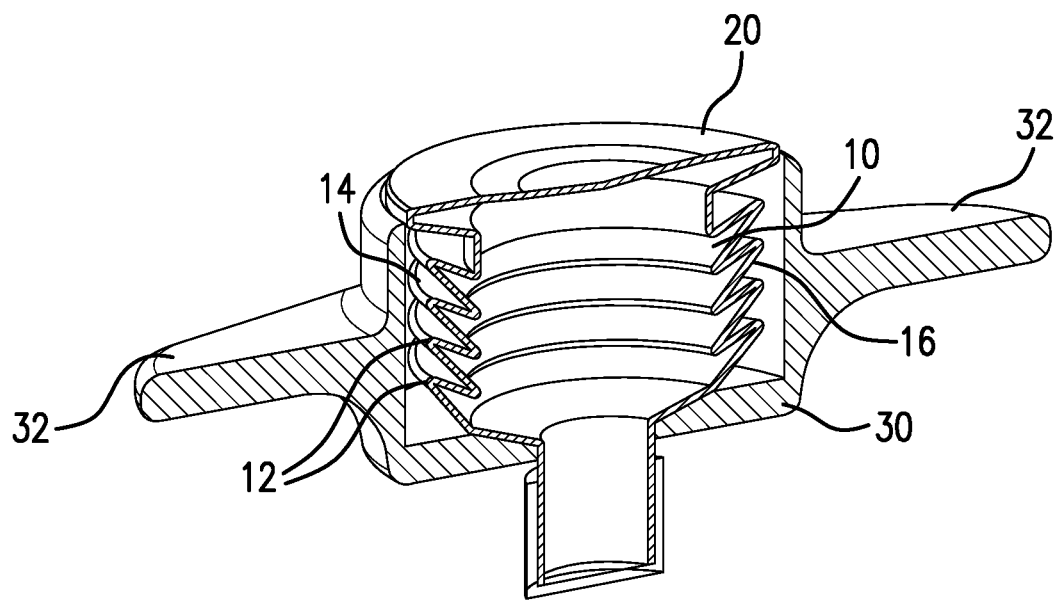
FIG. 6 is a cross-sectional view of an embodiment of the drug delivery device described herein, in its post-injection position or second position.

FIG. 6 shows a cross-sectional view of an embodiment of the drug delivery device described herein, in its post-injection position or second position. The embodiment of the drug delivery device shown in FIG. 6 has a drug container 10 comprising bellows 12, wherein the bellows have a first surface 14 and a second surface 16. The first surface 14 is in the shape of a first Belleville spring and the second surface 16 is in the shape of a second Belleville spring. In FIG. 6, drug container 10 also has top 20. Top 20 is axially aligned with the bellows 12. In FIG. 6, an axial force has been applied to top 20, causing the first Belleville spring to deflect. As shown in FIG. 6, there is minimal residual space remaining in the drug container 10, thus ensuring that entire amount of drug that was in the drug container 10 in its pre-injection position or first position has been dispensed.

Additionally, when compressed in the post injection or second position, the first Belleville spring is stable and requires an equal but opposite axial force to expand back to its post-injection or first position. This prevents the drug delivery device from being reused or refilled. Also shown in FIG. 6 is housing 30. The housing 30 has a pair of flanges 32.

Figure 7:
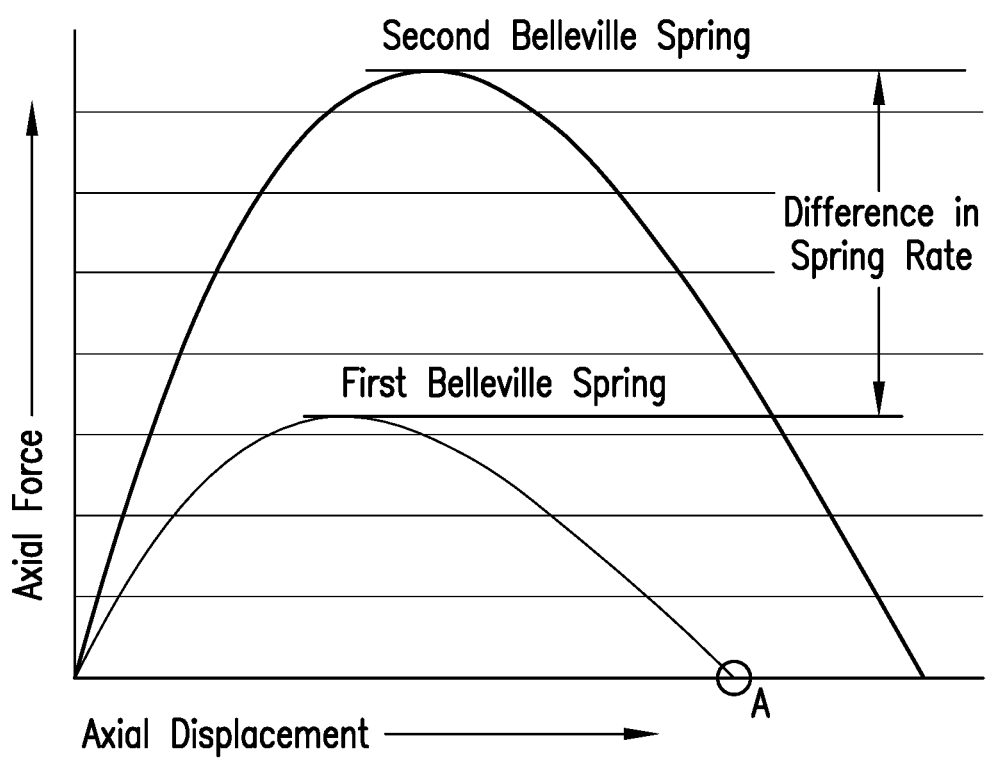
FIG. 7 is a graph showing applied axial force versus axial displacement of the first Belleville spring and the second Belleville spring.

FIG. 7 shows applied axial force versus axial displacement of the first Belleville spring and the second Belleville spring. As shown in FIG. 7, a greater axial force is needed to displace the second Belleville spring. Thus, the second Belleville spring has a higher spring rate than the first Belleville spring. As shown in FIG. 7, less axial force is needed to displace the first Belleville spring as compared to the second Belleville spring. At point A on the axial displacement in FIG. 7, the first Belleville spring is in its post-injection or second position and is locked and requires an equal but opposite axial force to expand back to its post-injection or first position. This prevents the drug delivery device from being reused or refilled.

Figure 8:
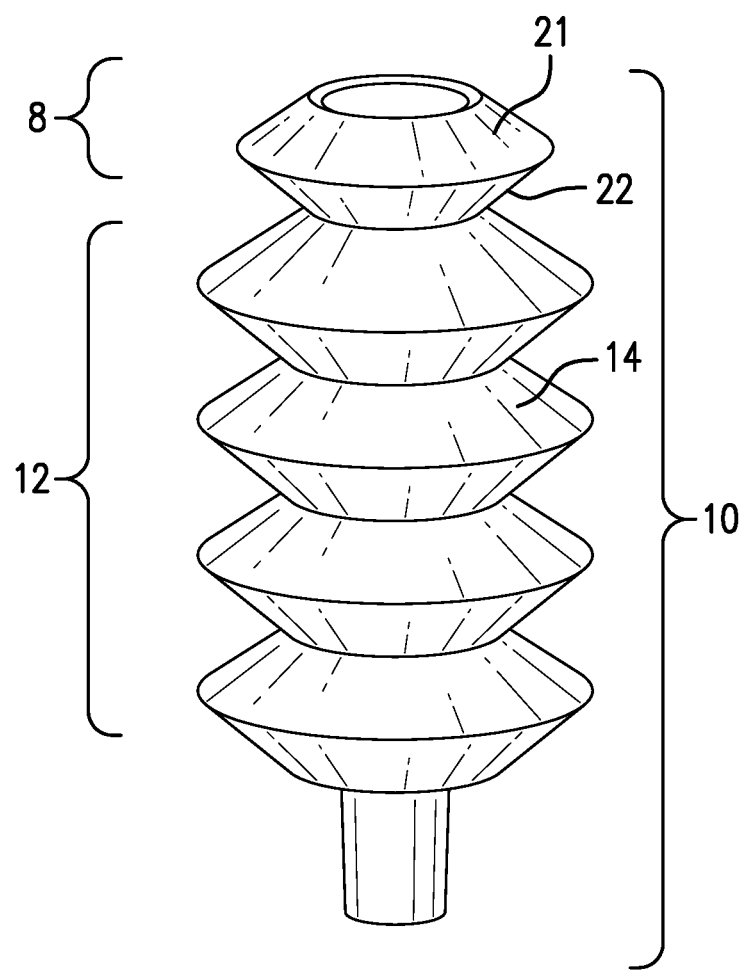
FIG. 8 is a perspective view of an embodiment of a drug container comprising an additional bellow for priming purposes.

FIG. 8 is a perspective view of an embodiment of the drug delivery device described herein, with a drug container 10 comprising a priming bellow 8. The priming bellow 8, requires less force to compress than bellows 12 in the drug container 10, whereby application of compressive force to the drug container 10 causes the priming bellow 8 to compress first. In this embodiment, priming bellow 8 can function to evacuate trapped air or other fluid from the drug container 10 prior to dispensing of the drug. In a certain embodiments, priming bellow 8 comprises a first Belleville spring 21 and a second Belleville spring 22. The first Belleville spring 21 of the priming bellow 8 has a lower spring rate than the first Belleville spring 14 of bellow 12. In an exemplary embodiment, the first Belleville spring 21 and second Belleville spring 22 of the priming bellow 8 have a lower spring rate than that of the first Belleville spring 14 of bellows 12 in drug container 10. In an exemplary embodiment, the outer diameter of priming bellow 8 is different from the outer diameter of bellows 12.

Figure 9:
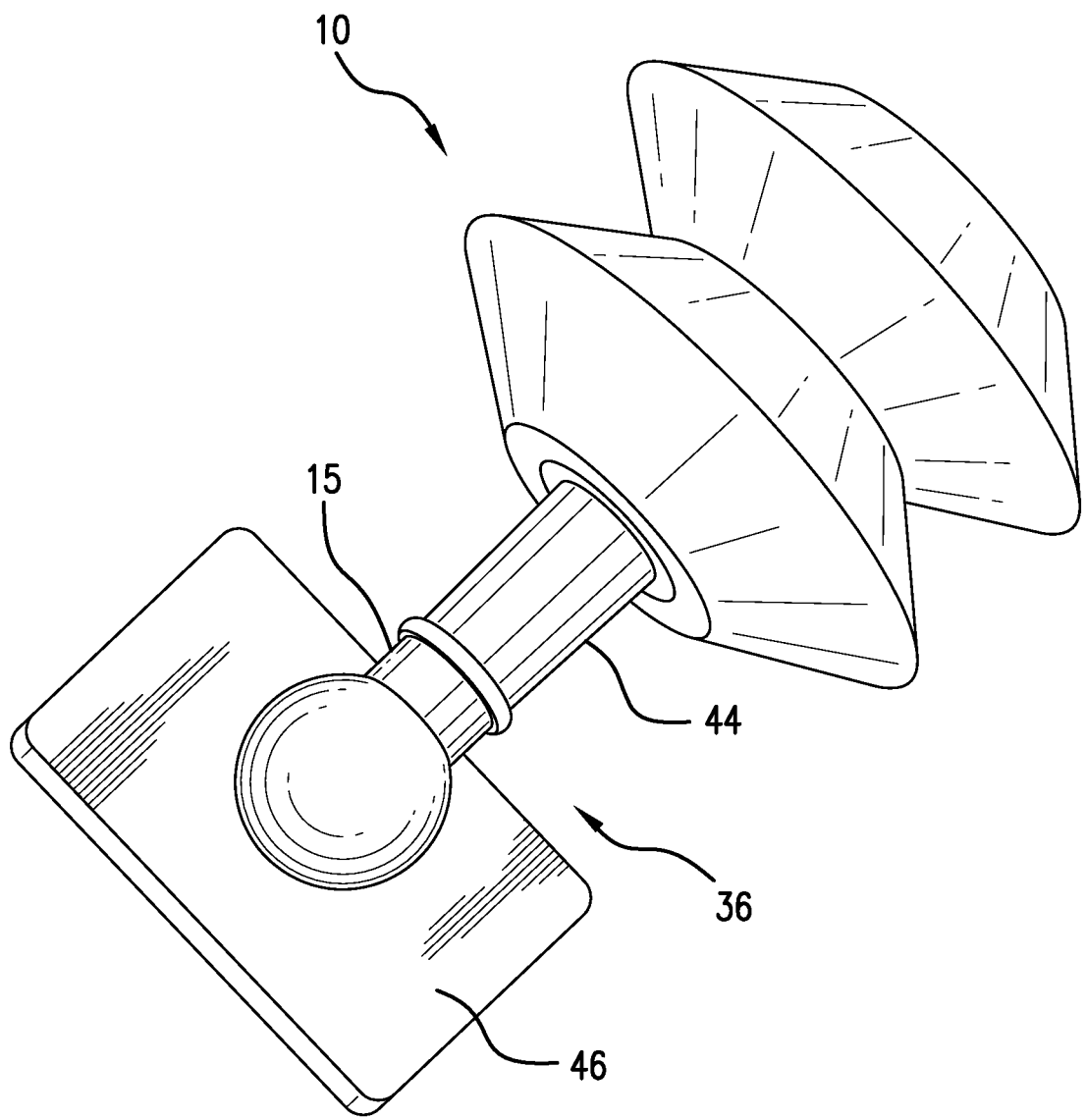
FIG. 9 is a detail view of the distal end of a drug container, and a frangible seal employing a twist-off tab.

FIG. 9 is a detail perspective view of the distal end 36 of the drug container 10. The drug container 10 comprises an outlet port 15. Outlet port 15 has a Luer taper 44 for connecting needle to the drug container 10. In FIG. 9, drug container 10 is manufactured with an integrally molded, twist-off tab 46 at its distal end 36. Removal of said tab 46 opens the distal end 36 of the drug container 10 for dispensing of the drug contained within drug container 10.

In certain embodiments, when tab 46 is removed a needle hub has access to appropriate geometry for attachment of a needle with a mating Luer geometry. In another embodiment, a film or foil seal can be removed from the opening on the drug container's distal end for dispensing of the drug. In another embodiment, the distal end of the drug container can be pierced by an extension of the needle in the proximal direction, so that the needle pierces the distal end of the drug container when it is secured to the drug container. In an alternate embodiment, the distal end of the drug container is manually pierced or cut off by the user prior to use. In certain alternate embodiments, the drug delivery device described herein further comprises a needle in communication with the outlet port of the drug container.

Figure 10:
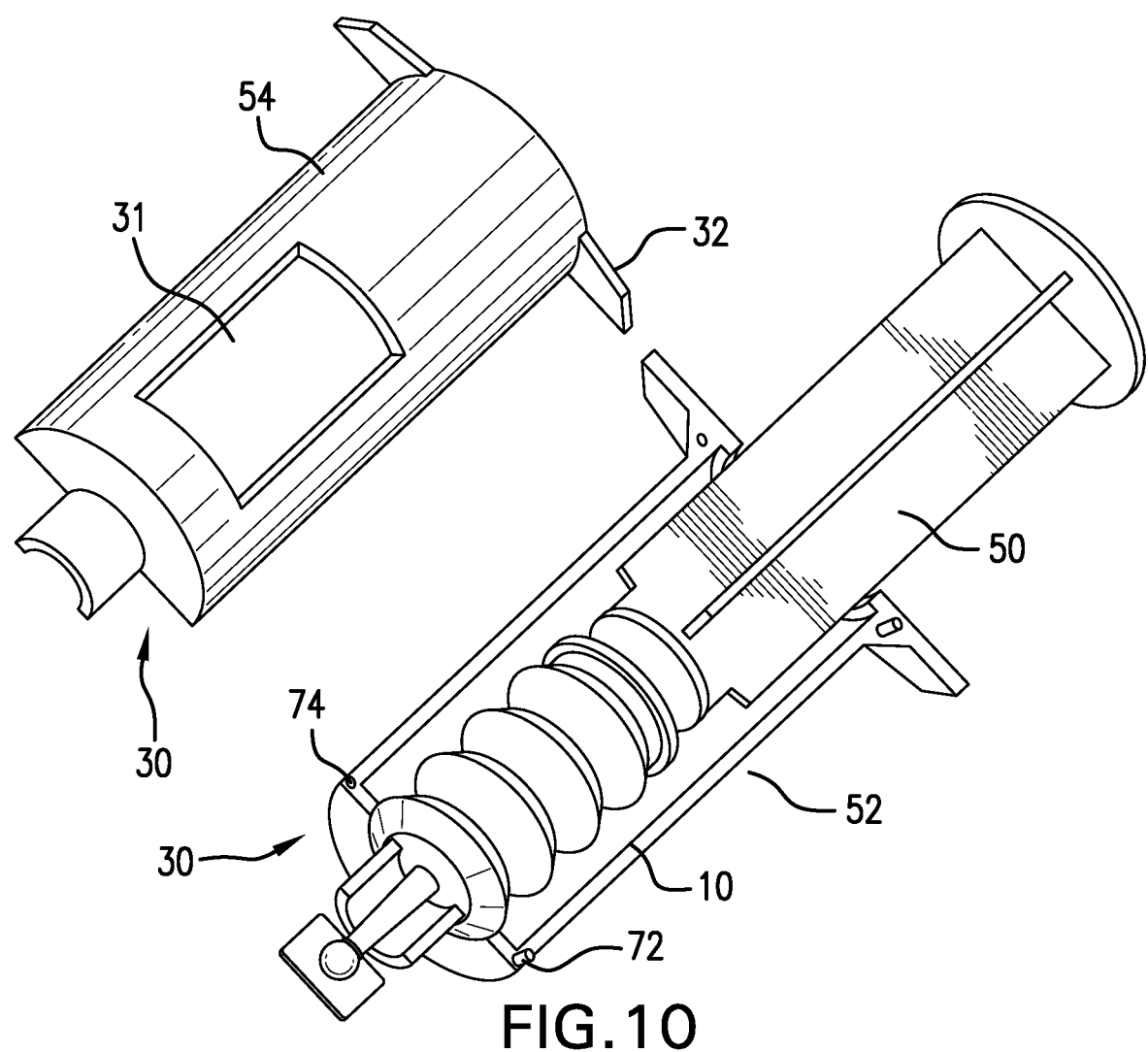
FIG. 10 is an exploded view of a drug delivery device comprising a drug container, a housing, and a plunger.

FIG. 10 is a exploded view of an embodiment wherein the drug container 10 is fully contained within a housing 30, and wherein the compressive force is applied to the drug container 10 by a plunger 50. In FIG. 10, housing 30 comprises flanges 32. Plunger 50 can move axially within housing 30, and is retained within the housing 30 so it cannot be removed. In FIG. 10, housing 30 comprises a first half 52 and a second half 54. The housing halves 52 and 54 comprise alignment features for locating and aligning the first half 52 and second half 54 of the housing. As shown in FIG. 10, the engagement comprises locating pins 72 and mating holes 74. In alternate embodiments, other means of locating the two halves may be used, comprising tabs and slots, stepped surfaces, ribs, or any combination thereof. In FIG. 10, the first half 52 and second half 54 of housing 30 are identical to one another. In an alternate embodiment, the first half and second half of the housing are not identical to one another. In FIG. 10, housing 30 incorporates a view port 31 for visualizing the contents of the drug container.

Figure 11:
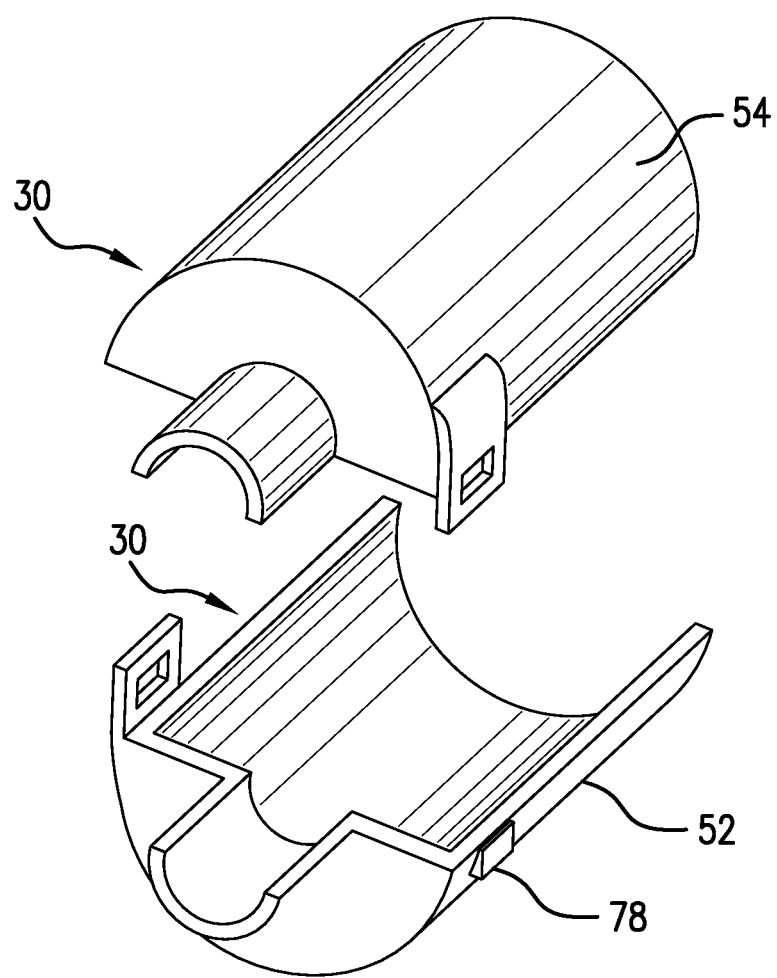
FIG. 11 is a detail view showing features for aligning the housing halves and holding them together.

FIG. 11 is a detailed view of a latch feature in housing 30, according to one embodiment of the drug delivery devices described herein. This figure shows latching geometry 78, which creates a snap fit that holds the first half 52 and second half 54 of the housing together. In certain embodiments, the latching geometry is also capable of engaging and retaining the drug container at its distal end. In an alternate embodiment, housing halves may be held together by one or more tensile bands. In an alternate embodiment, housing halves may be held together by one or more adhesive labels.

Figure 12:
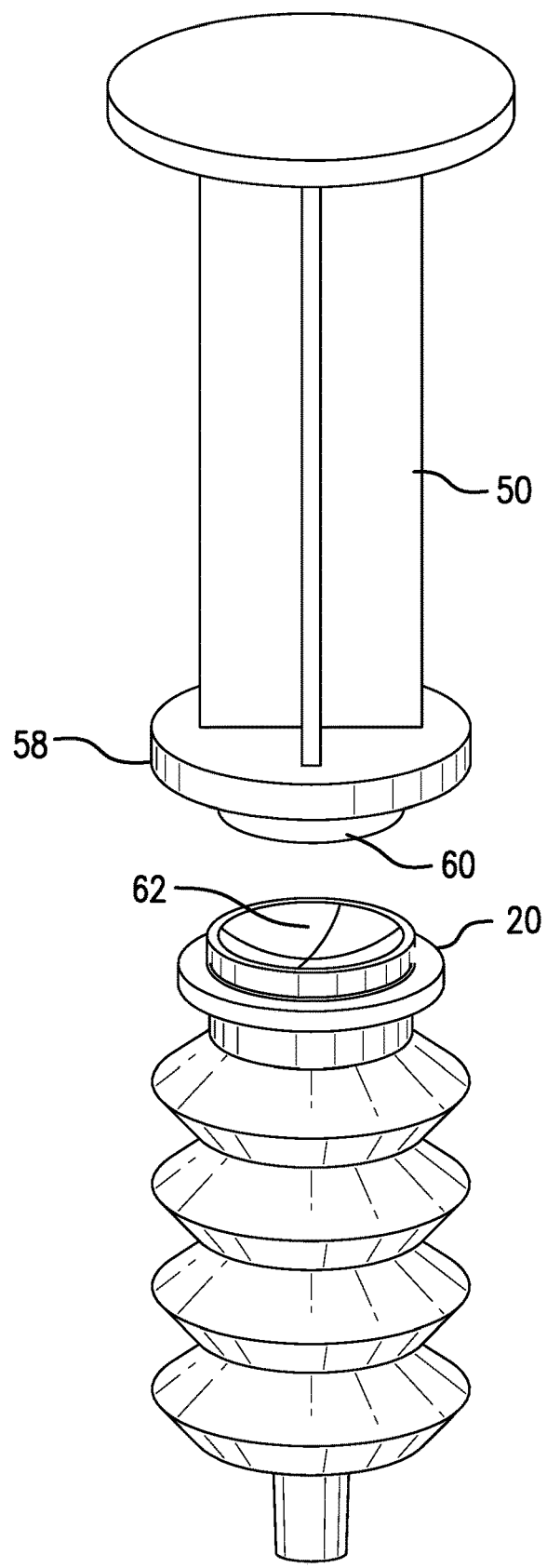
FIG. 12 is a detail view of a plunger and drug container with mating surfaces shaped to provide secure side-to-side engagement between them.

FIG. 12 shows an embodiment of the engagement of the plunger 50 and the drug container 10, wherein plunger 50 engages the top 20 of the drug container 10, wherein plunger 50 comprises a distal end 58 with a generally convex shape 60 and the top 20 of the drug container 10 comprises a mating concave shape 62, whereby the plunger 50 and the drug container 10 engage one another whereby they are axially aligned. In an alternate embodiment, the plunger comprises a distal end with a generally concave shape and the top of the drug container comprises a mating convex shape. It should be obvious to a skilled observer that many other alternate embodiments of an alignment feature may be employed, including a pin and hole, wherein the mating features may be cylindrical, conical, or polygonal in cross section, or multiple mating features.

Figure 13:
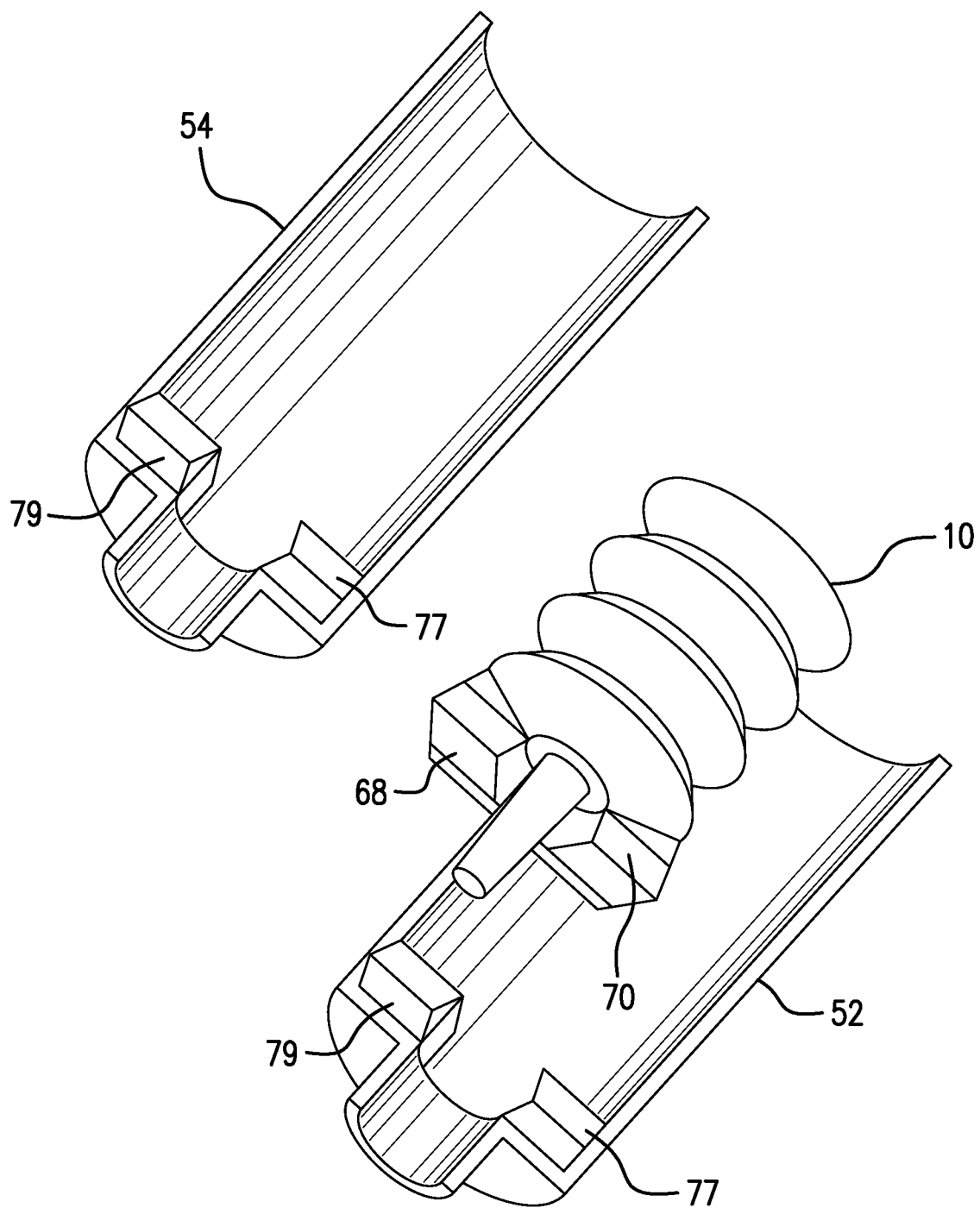
FIG. 13 is a detail view of securing features that align and secure the drug container in place when the two halves of the housing are assembled.

FIG. 13 shows drug container securing means wherein drug container comprises securing means comprising one or more features that align and secure the drug container in position when housing halves are secured together. In FIG. 13, the securing means comprises intersecting planes 68 and 70 located on drug container 10 and intersecting planes 77 and 79 located on housing half 52 and housing half 54, wherein these planes mate. In an alternate embodiment, the securing means comprises non-planar features that mate with matching features in housing first and second halves.

FIG. 13 shows a preferred embodiment, wherein the first securing means, intersecting planes 68 and 70 located on drug container 10 and intersecting planes 77 and 79 located on housing half 52 and housing half 54, are mirror images of one another to facilitate assembly without need for orientation of the drug container 10 during assembly.

Figure 14:
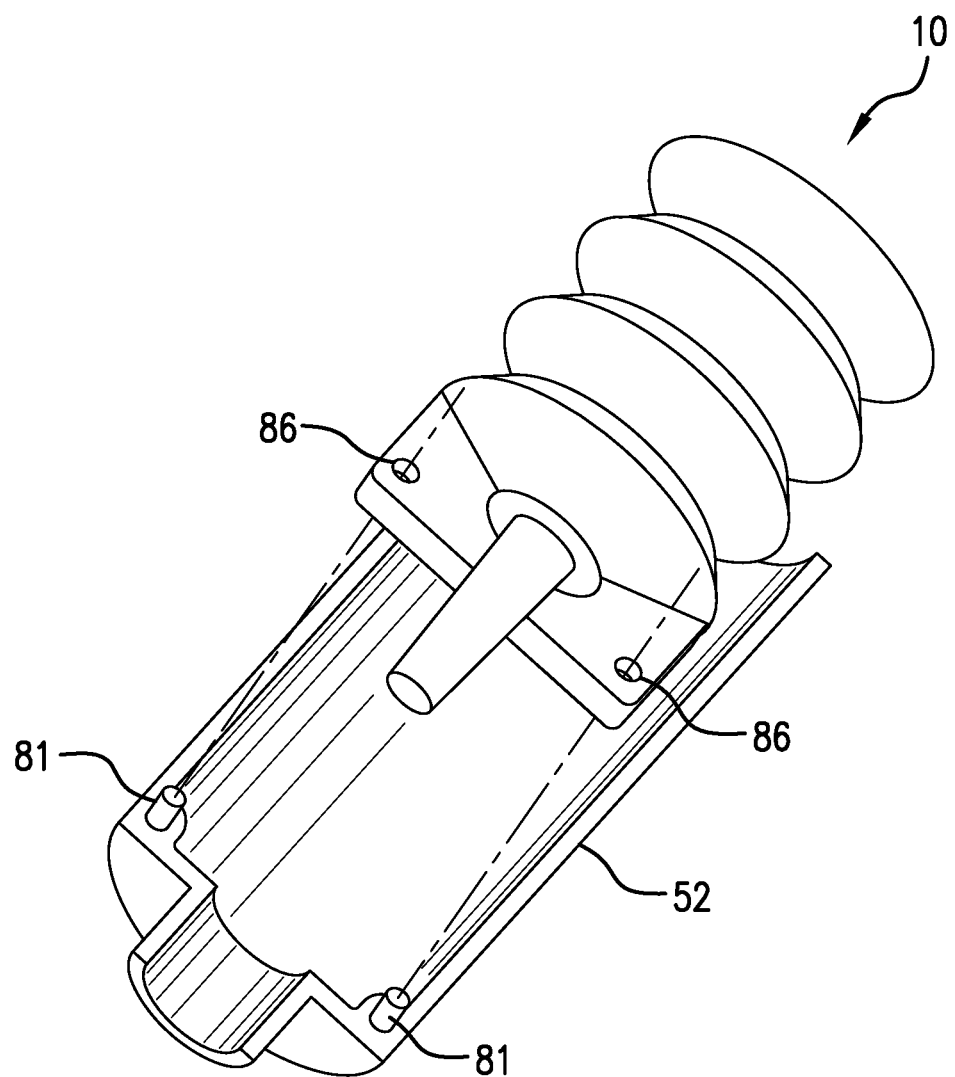
FIG. 14 is a detail view of engagement features of the drug container that are holes and mating pins.

FIG. 14 shows an alternate embodiment, wherein the the drug container 10 has holes 86 that engage with mating pins 81 located on housing half 52 as a means to secure drug container 10 to the housing.

Figure 15:
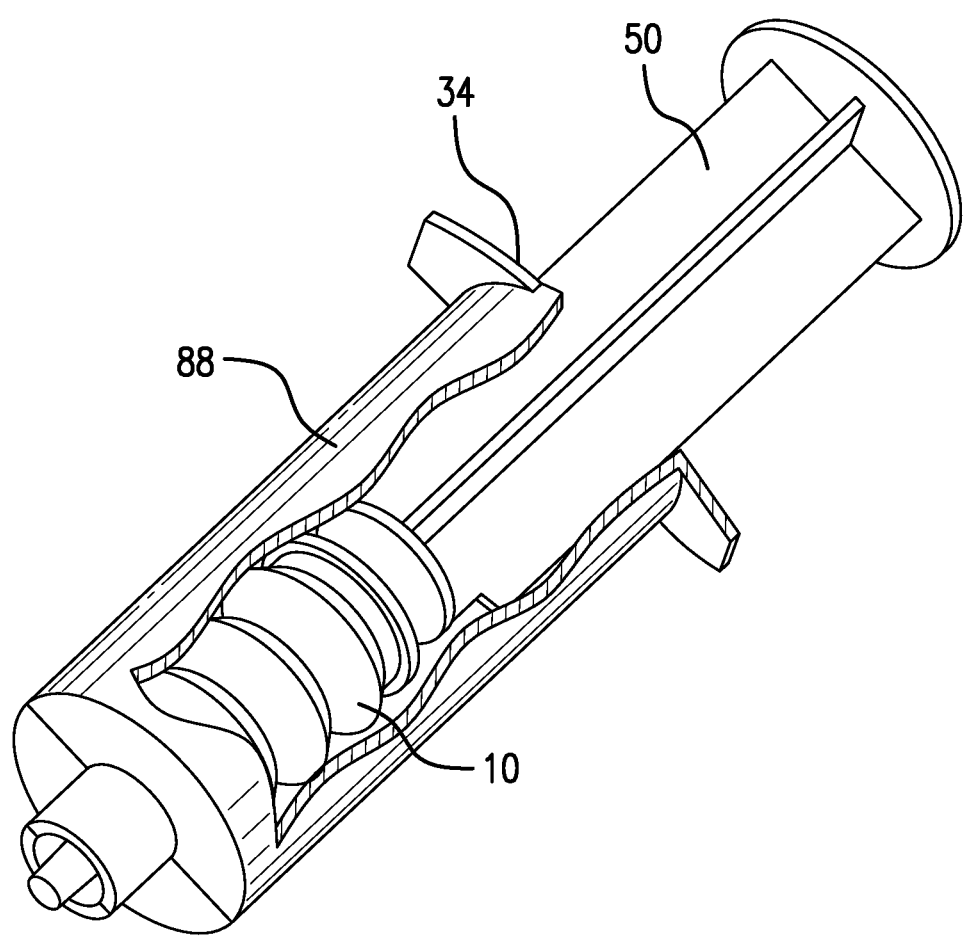
FIG. 15 is a cutaway view of an embodiment of a device comprising a one-piece housing

FIG. 15 is a cutaway view of an alternative embodiment, wherein the housing is comprised of a single part 88, and wherein the drug container 10 and the plunger 50 are assembled into the housing 88 from the proximal end 34.

Figure 16:
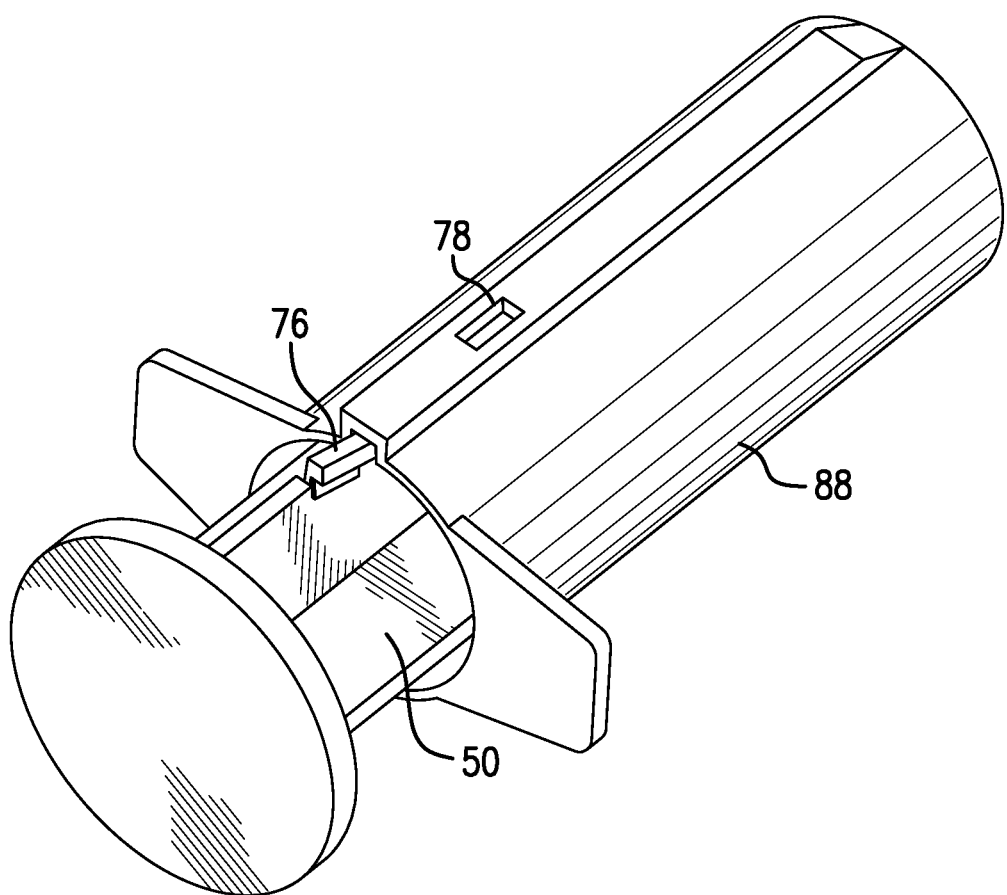
FIG. 16 is a detail view of an embodiment of the device comprising a one-piece housing with retention means to prevent withdrawal of the plunger from the housing.

FIG. 16 is a view of an exemplary embodiment of plunger retention means, whereby one or more projecting tabs 76 in plunger 50 engage mating recesses 78 in the one-piece housing 88. Tabs 76 are shaped to permit movement through recesses 78 in the distal direction, but prevent return movement of plunger 50 in the proximal direction. Recesses 78 can be located at one or more points along the length of housing 88 to control the movement of plunger 50.

Figure 17:
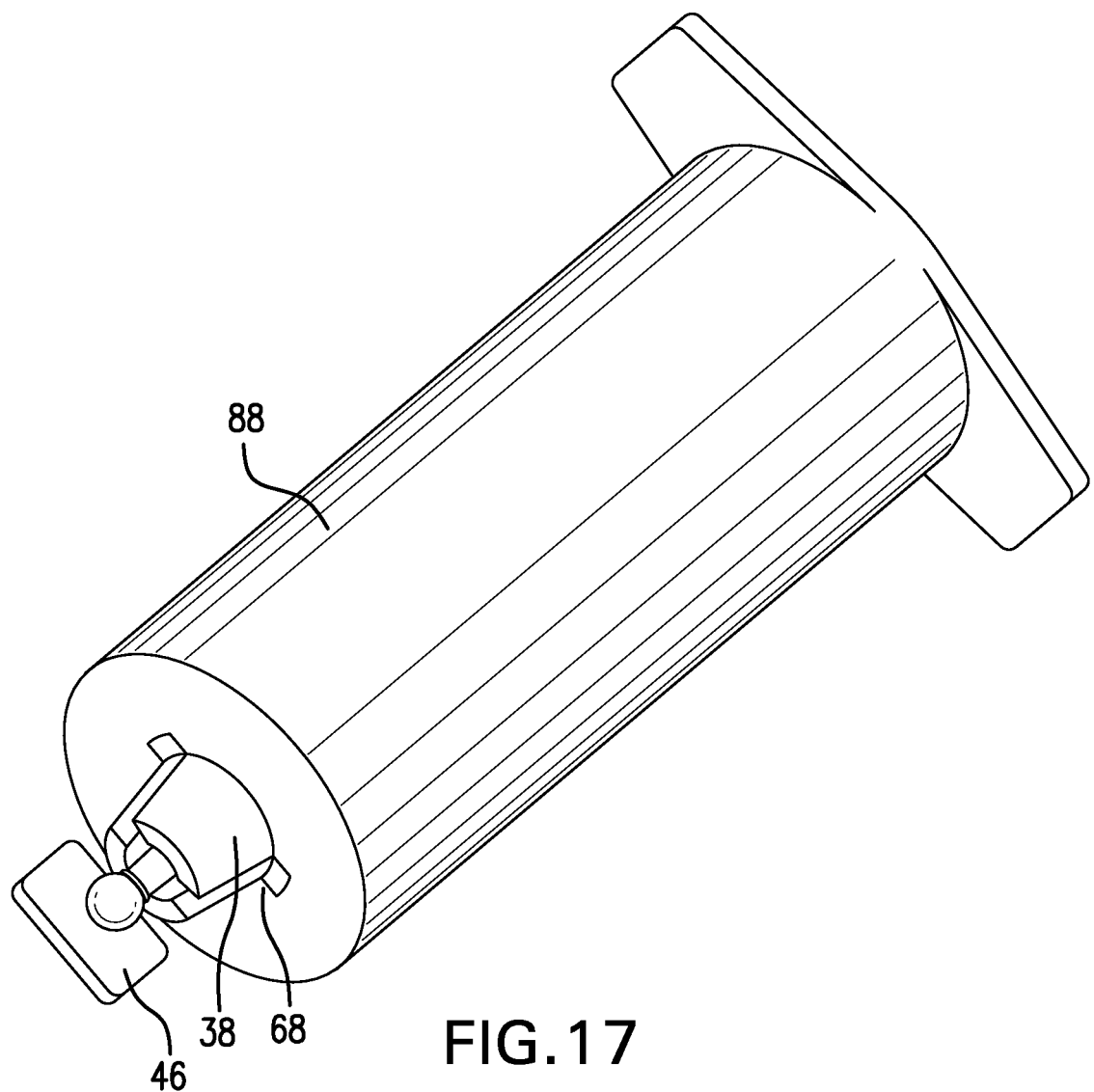
FIG. 17 is a detail view of an embodiment of the device comprising a one-piece housing with a slot through the distal opening to accommodate the twist-off tab of the drug container.

FIG. 17 shows an embodiment wherein the outlet port 38 of housing 88 comprises a slot 68 that bifurcates it. The slot 68 has sufficient cross sectional size to enable the twist off tab 46 to pass through the slot 68 during assembly.

Figure 18:
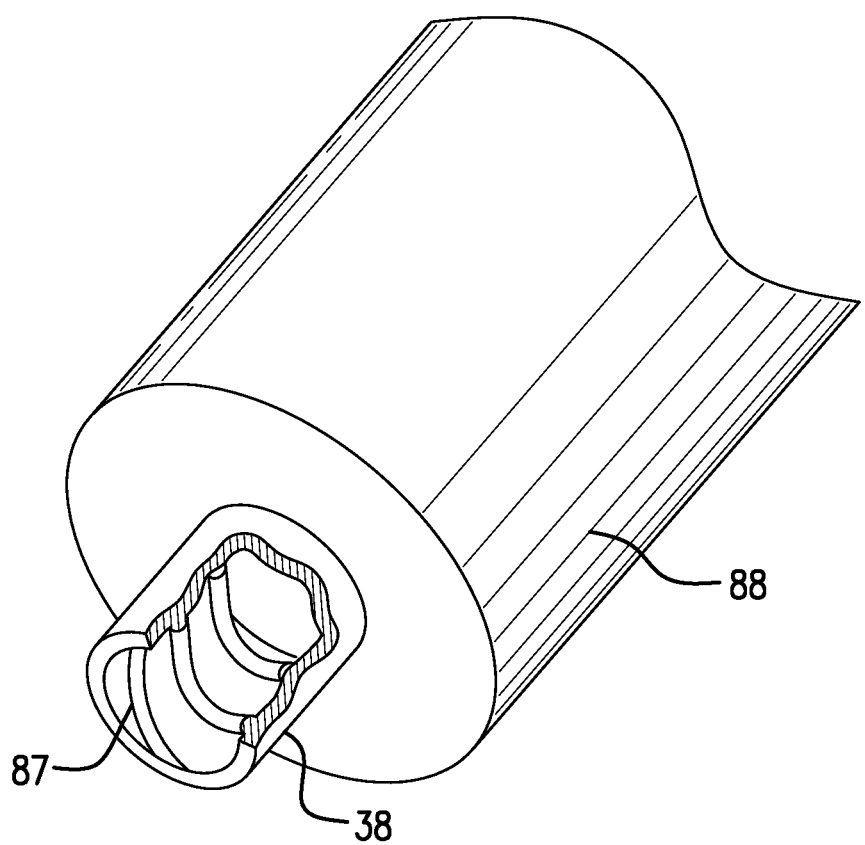
FIG. 18 is a detail view of an embodiment of the device showing threads for engaging a needle with a Luer connection.

FIG. 18 shows an embodiment wherein the outlet port 38 of housing 88 comprises internal threads 87 that engage with mating threads in the hub of an attachable standard Luer needle. In an alternate embodiment, the threads are other than Luer threads. In an alternate embodiment, the threads are external to the outlet port.

Figure 19:
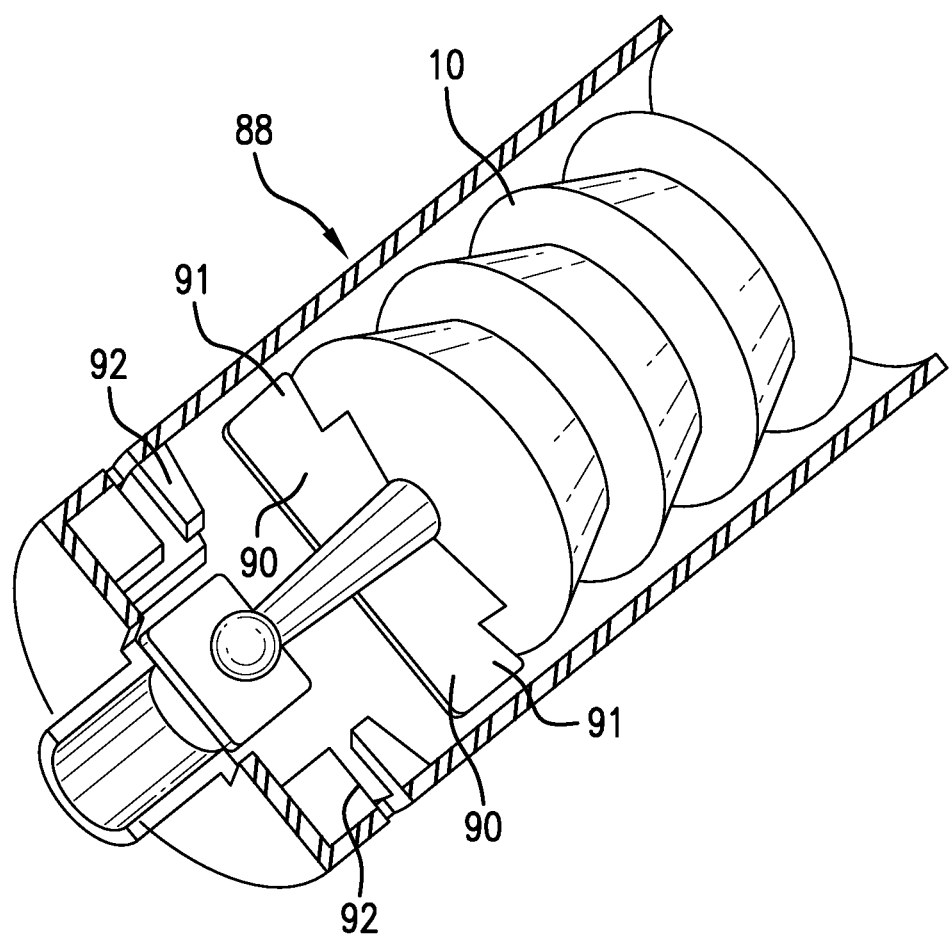
FIG. 19 is a view of an embodiment of the device comprising a one-piece housing and a drug container with securing tabs that engage mating features in the housing.

FIG. 19 shows an embodiment wherein the drug container 10 comprises one or more securing tabs 90 that engage mating receptacles in housing 88, wherein securing tabs 90 comprise flexible tabs 91 that flex to engage mating features 92 when drug container 10 is inserted into housing 88, wherein said features 91 prevent withdrawal of the dug container 10 in the proximal direction.

Figure 20:
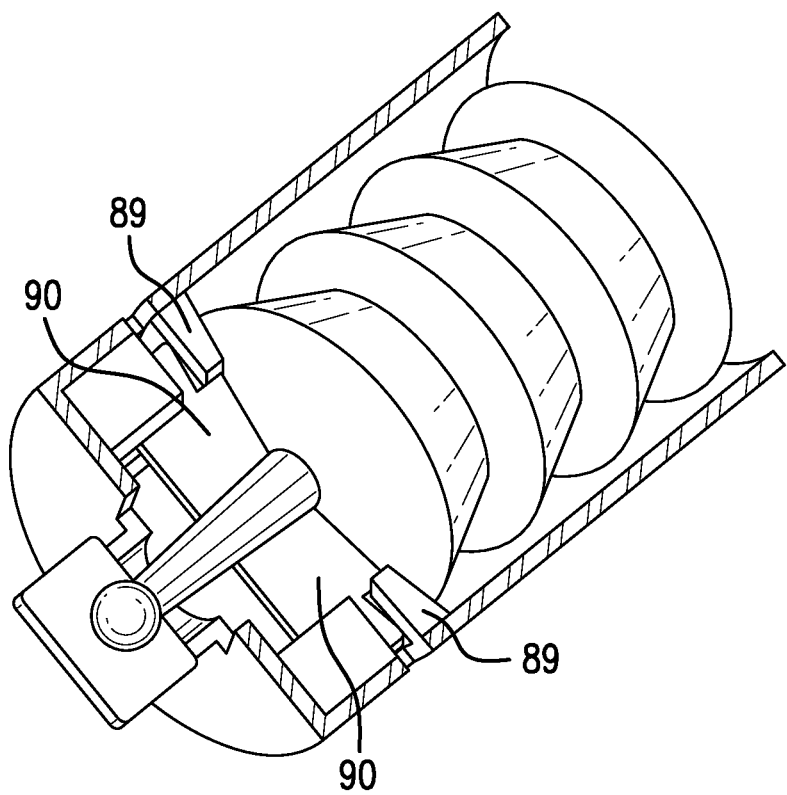
FIG. 20 is a view showing the drug container securing tabs engaged with the mating features in the housing.

FIG. 20 shows the securing tabs 90 engaged in mating receptables 89.

Figure 21:
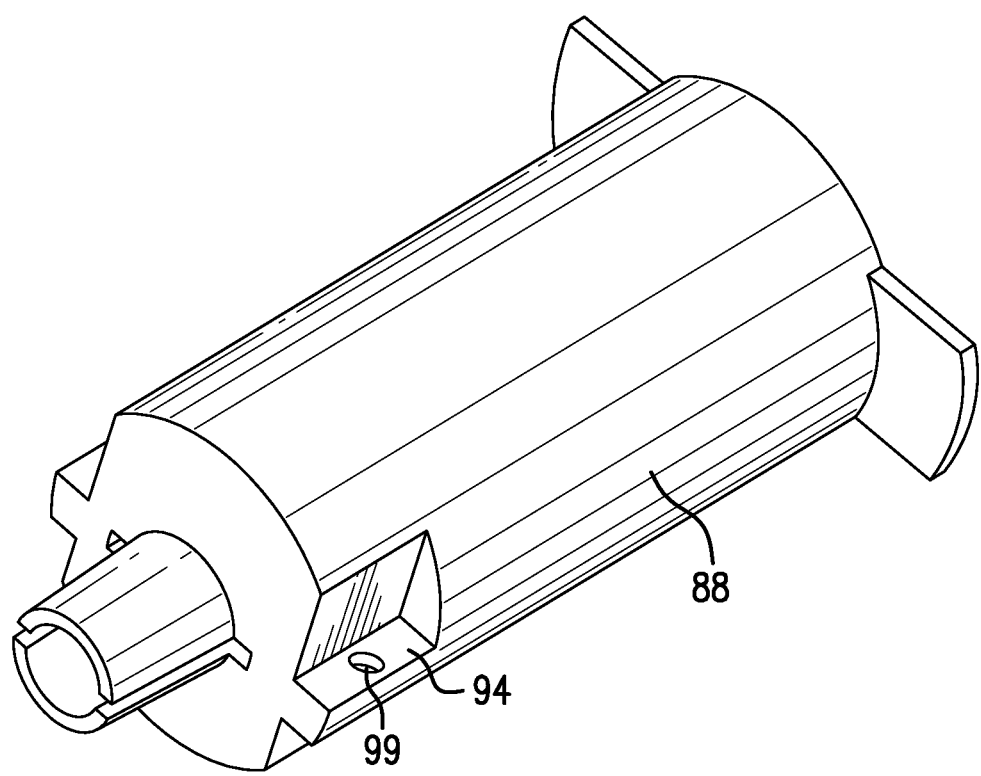
FIG. 21 is a view of an embodiment of the device comprising a means for securing the drug container in a one-piece housing my means of swaging.
Figure 22:
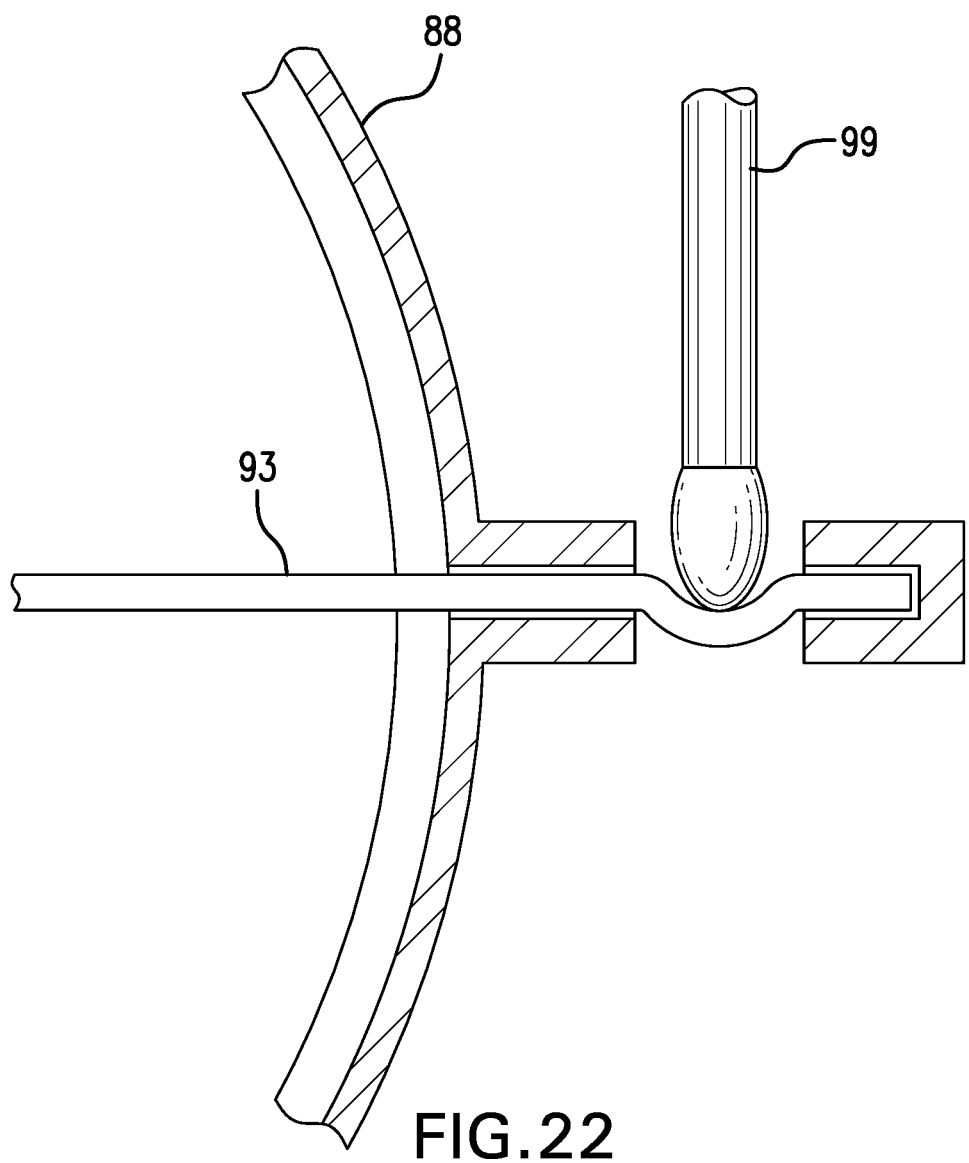
FIG. 22 is a detail view of a thermal swaging means for securing the drug container in the housing.

FIG. 21 shows an alternate embodiment, wherein receptacle 94 in one-piece housing 88 comprise openings through which the drug container securing means can be swaged in place. In the detail of the embodiment shown in FIG. 22, a thermal swaging tool 99 may be employed for swaging the securing means 93 in housing 88.

In an alternate embodiment, swaging of the drug container may be achieved through local mechanical deformation of the drug container. In an alternate embodiment, the securing means comprise holes that align with the holes in the housing when the drug container is fully seated in the housing. The aligned holes may be filled with a fixative such as a hot melt adhesive to secure the drug container in position. In an alternate embodiment, the drug container is secured in the housing with attachment means comprising pins or rivets that are swaged or snapped into place.

Figure 23:
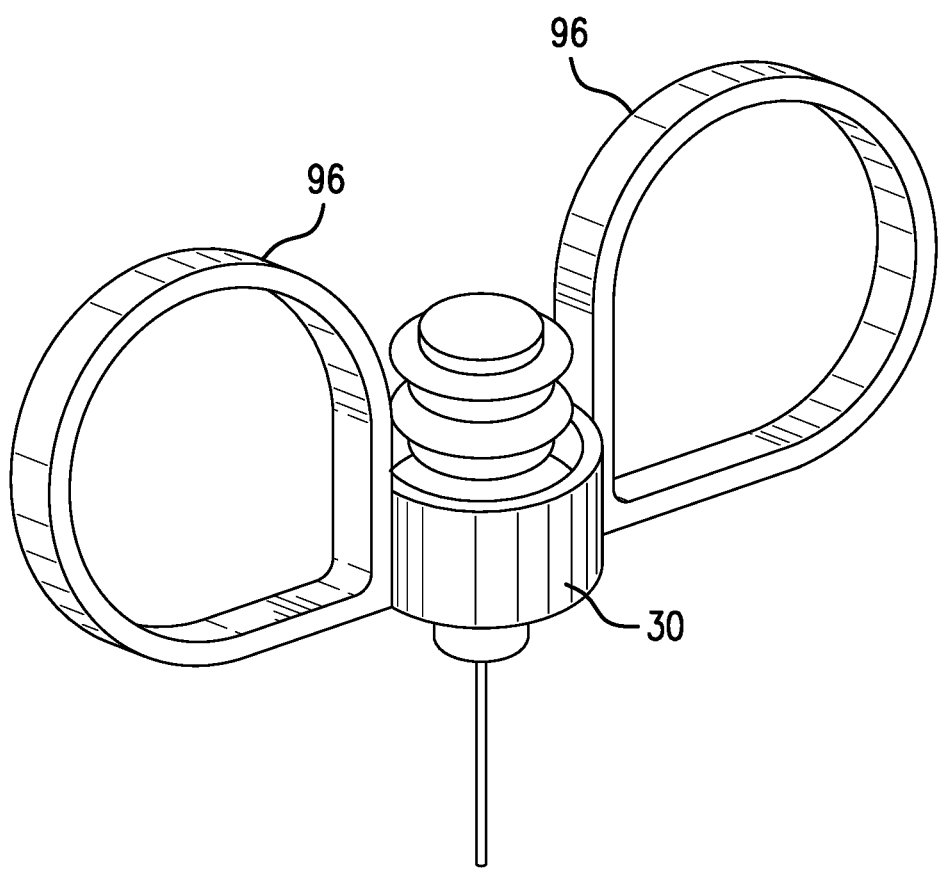
FIG. 23 is a view of a device comprising a housing with fully closed flanges for receiving the user's fingers.

FIG. 23 shows a drug delivery device with a housing 30 that comprises fully enclosed finger flanges 96 for receiving the user's fingers.

Figure 24:
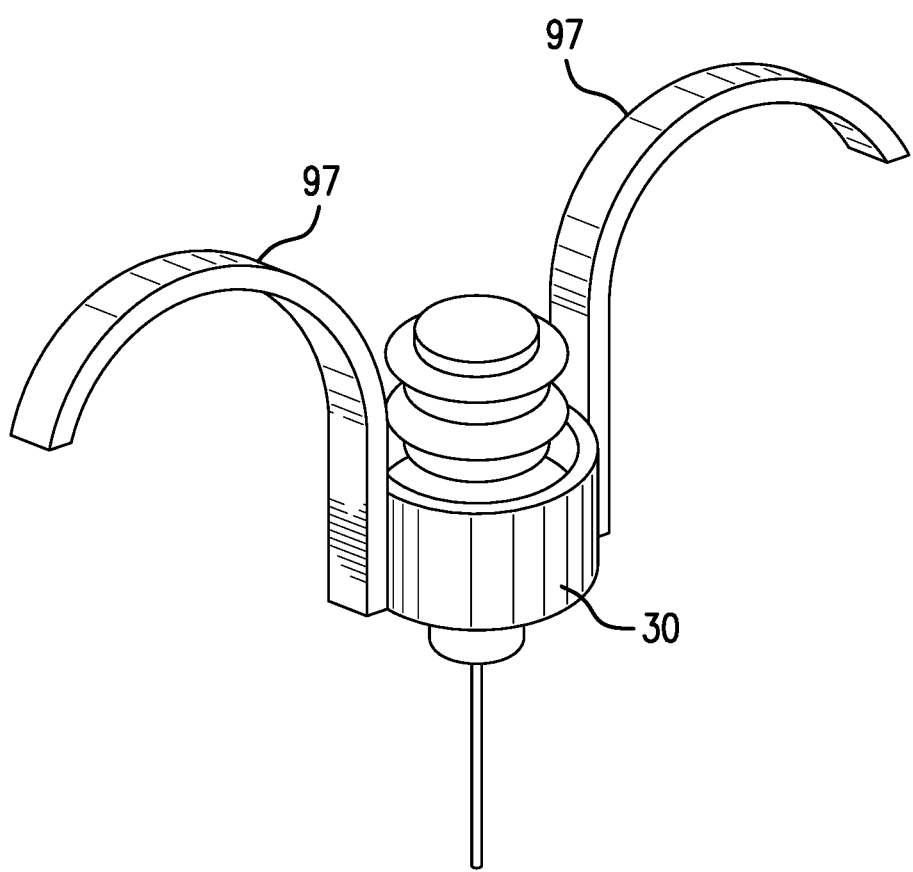
FIG. 24 is a view of an embodiment of a device comprising a housing with partially closed flanges for receiving the user's fingers

FIG. 24 shows a drug delivery device with a housing 30 that comprises partially enclosed finger flanges 97 for receiving the user's fingers.

Figure 25:
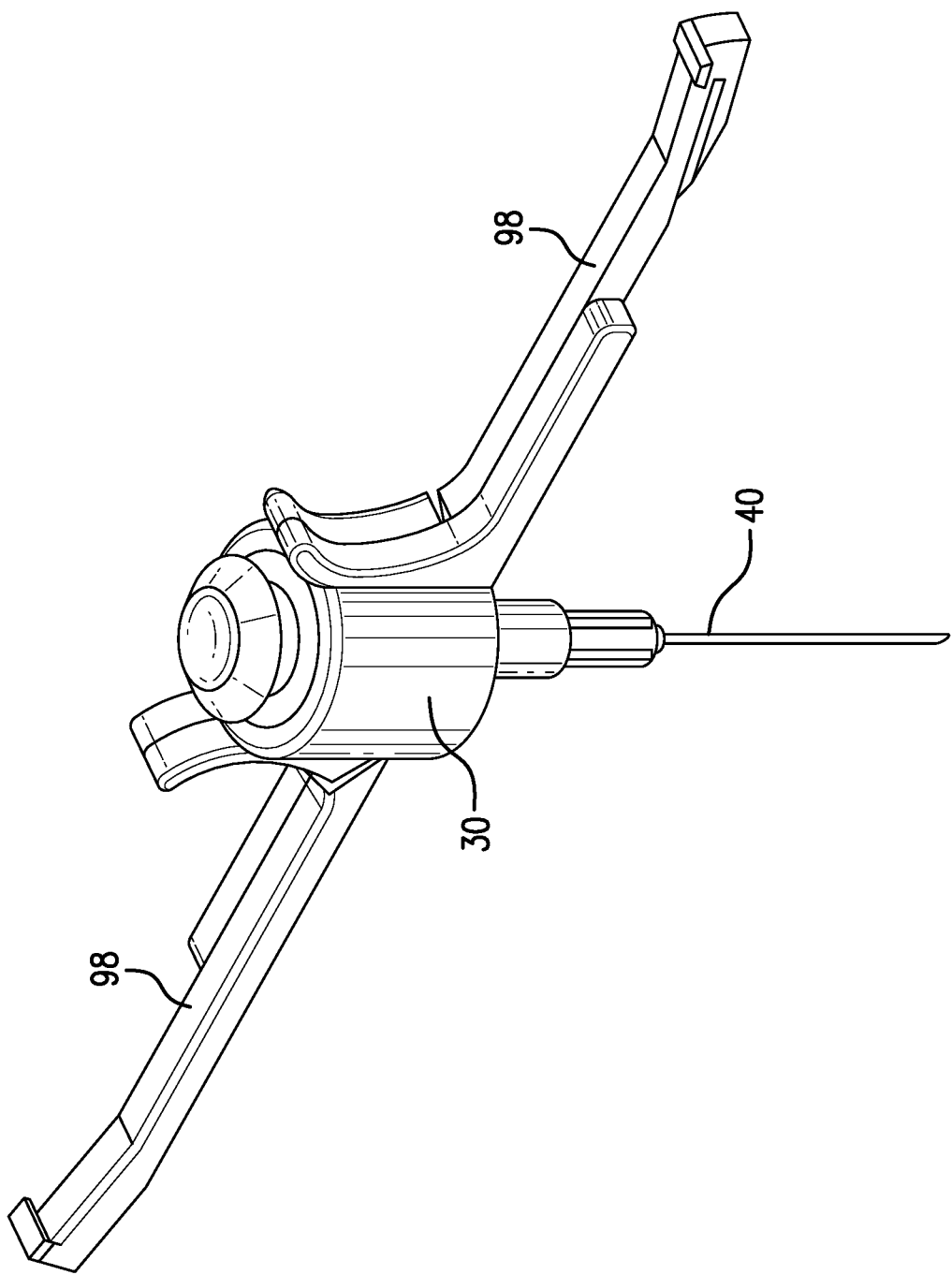
FIG. 25 is a perspective view of an embodiment of a device comprising a housing with hinged flanges that can be swung in the distal direction after injection and removal of the device, to protect the needle.

FIG. 25 is a perspective view of an embodiment of a device comprising a housing 30 with hinged flanges 98. Prior to and during injection of the drug, the hinged flanges 98 are oriented for gripping the device with two fingers of one hand. After injection of the drug and removal of the device from the patient, the hinged flanges 98 can be swung in the distal direction to shield the needle 40, as shown in FIG. 26.

Figure 26:
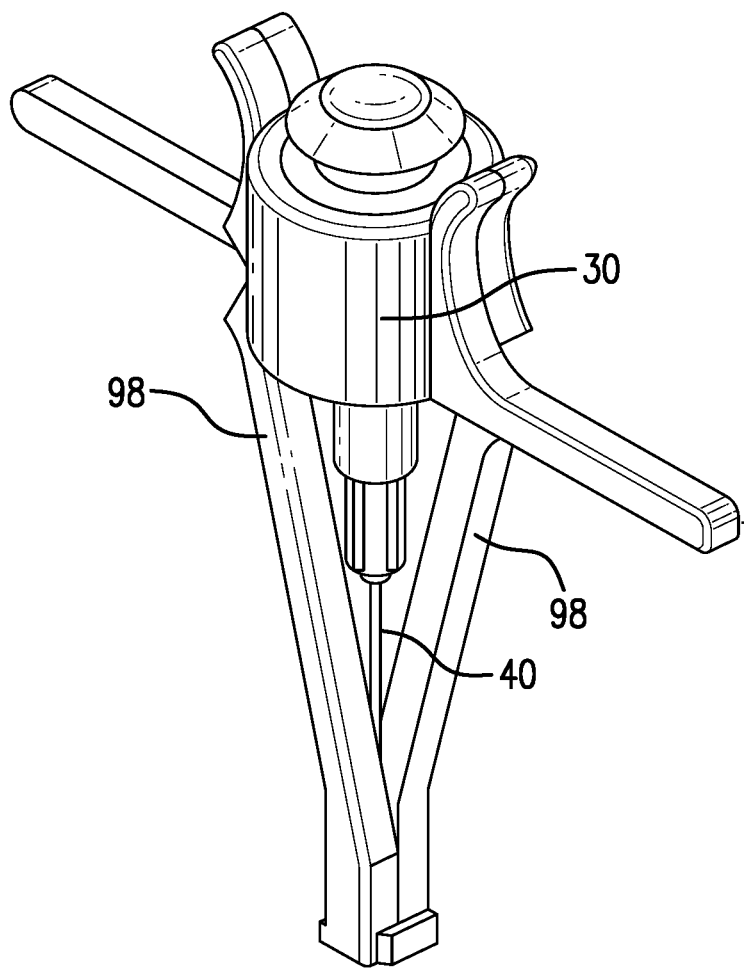
FIG. 26 is a perspective view of a device comprising a housing with hinged flanges that have been can be swung in the distal direction to protect the needle.

FIG. 26 is a perspective view of a device comprising a housing 30 with hinged flanges 98 that have been can be swung in the distal direction to protect the needle 40. The flanges may comprise one of several hinging means, including ball and socket joint, a pin joint, or a living hinge 100 as shown in FIG. 27.

Figure 27:
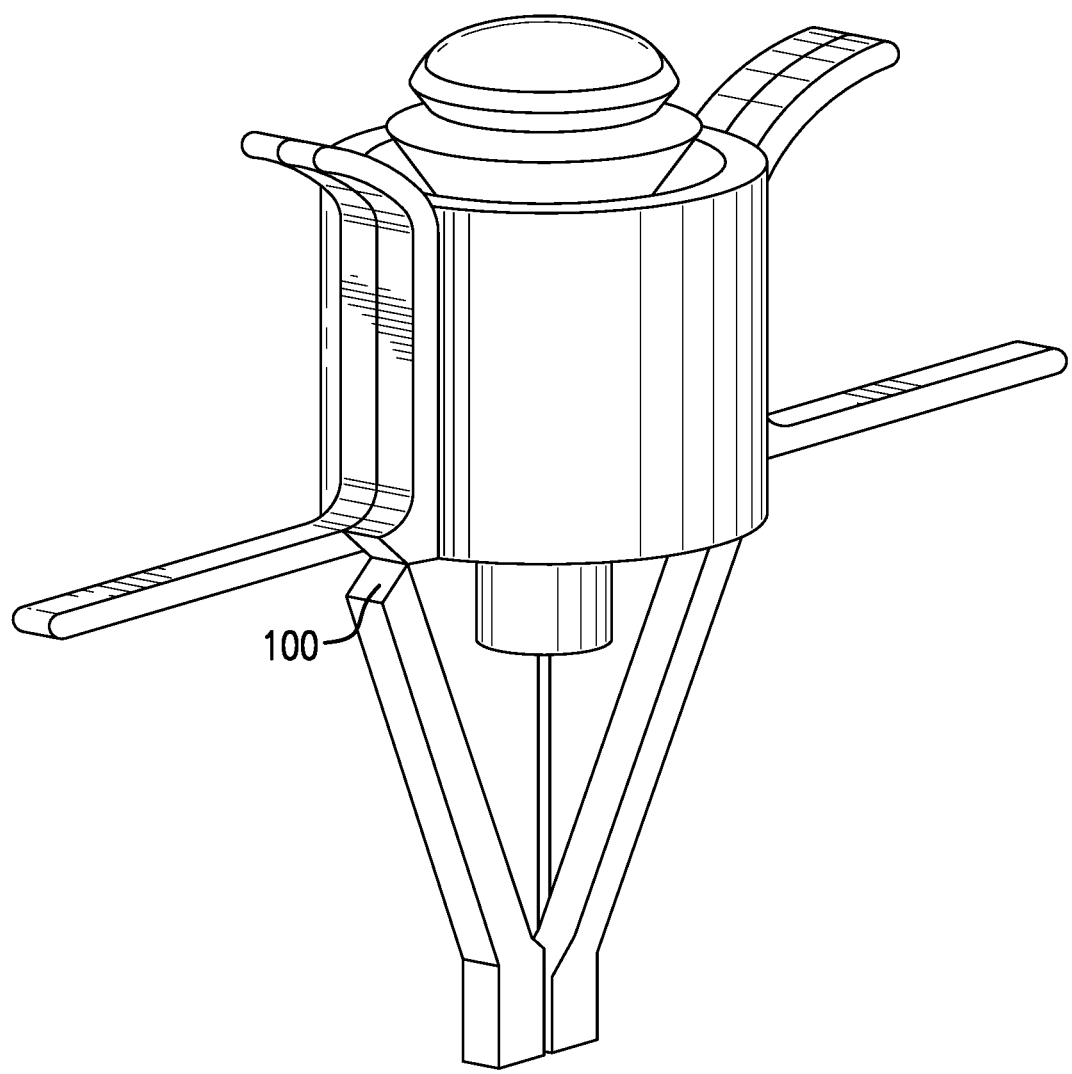
FIG. 27 is a view of a hinged flange comprising a living hinge.

FIG. 27 is a view of a hinged flange comprising a living hinge 100.

The drug delivery device can be used to deliver any type of drug product that can be delivered via a syringe. In certain embodiments of the drug delivery device described herein, the drug container contains In certain embodiments of the drug delivery device described herein, the drug in the drug container may comprise one or more of the following: human papillomavirus quadrivalent vaccine, recombinant; human papillomavirus 9-valent vaccine, recombinant; haemophilus B conjugate vaccine or meningococcal protein conjugate; hepatitis B vaccine, recombinant; haemophilus B conjugate; hepatitis B (recombinant) vaccine; hepatitis A vaccine, inactivated; pneumococcal vaccine polyvalent; artemether; cyclimorph (morphine and cyclizine); cyclizine; morphine; codeine; chlorphenamine; fosphenytoin sodium; chlorpromazine; haloperidol; epinephrine; hydroxocobalamin; heparin sodium; phytomenadione; atropine; furosemide; lidocaine; dalteparin sodium; digoxin; amiodarone; dextran 70; polygeline; hyoscine hydrobromide; oxytocin and ergometrine; oxytocin; carbetocin; magnesium sulfate; dexamethasone; metooclopramide; ondansetron; ketamine; neostigmine; pyridostigmine; dimercaprol; ranitidine; testosterone; calcium gluconate; diazepam; acetylcysteine; sulfamethoxazole+trimethoprim; hydroxocobalamin; protamine sulfate; tranexamic acid; verapamil; anti-D immunoglobulin (human); diphtheria antitoxin; suxamethonium; fluphenazine; salbutamol; pediatric hexavalent combination vaccine for *Haemophilus influenzae* type B conjugate, recombinant hepatitis B surface antigen, diphtheria, tetanus, 5-component acellular pertussis, and inactivated poliovirus Types 1, 2, and 3; BCG Vaccine; cholera vaccine; diphtheria vaccine; *Haemophilus influenzae* type B vaccine; influenza vaccine; Japanese encephalitis vaccine; measles vaccine; meningococcal meningitis vaccine; mumps vaccine; pertussis vaccine; pneumococcal vaccine; poliomyelitis vaccine; rabies vaccine; rotavirus vaccine; rubella vaccine; tetanus vaccine; typhoid vaccine; varicella vaccine; yellow fever vaccine. In certain embodiments of the drug delivery device described herein, the drug container is pre-filled with a drug such as oxytocin or carbetocin.

Also described herein are methods of manufacturing the drug delivery devices described herein. The drug container may be produced using a variety of manufacturing methods. In certain embodiments, the drug container is manufactured by blow-fill-seal technology (BFS). In other embodiments, the drug container is manufactured by form-fill-seal technology (FFS).

In preferred embodiments, the drug container is made of thin flexible plastic. The drug container and housing of the delivery devices described herein are preferably made of a biocompatible, non-biodegradable polymer. Suitable biocompatible, non-biodegradable polymers include but are not limited to, a polyacrylate; a polymer of ethylene-vinyl acetate; an acyl-substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; a polyethylene; a polypropylene; a metallocene plastomer, a thermoplastic elastomer, an acrylic, a polycarbonate, an acrylonitrile-butadiene-styrene, a multi-layer barrier film; or a blend, combination, or copolymer thereof. Each component of the drug delivery device described herein can be made of the same or different biocompatible, non-biodegradable polymer. In certain embodiments, a multi-layer barrier film may be used, depending on drug container performance requirements. It should be obvious to those skilled in the art that most of these alternate embodiments may be combined to create a drug container with desired attributes suitable for specific applications.

The embodiments illustrated and discussed in this specification are intended only to teach those skilled in the art the best way known to the inventors to make and use the invention. Nothing in this specification should be considered as limiting the scope of the present invention. All drawings presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A pre-filled drug delivery device comprising:
a drug container having a volume and containing a drug, wherein the drug container comprises an outlet port and at least one bellow, wherein each bellow of the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring;
wherein the drug container has a pre-injection position or first position, and a post-injection position or second position, wherein in the first position, the drug container is extended axially to its full length, wherein the at least one bellow is expanded, and wherein the volume contained within the drug container is maximized and in the second position, the drug container is compressed axially to its minimum length, wherein the at least one bellow is compressed, such that the first Belleville spring is inverted and nested inside of the second Belleville spring, and wherein the volume contained within the drug container is minimized;
wherein when the drug container is in the second position, the drug container has dispensed the drug and due to the first Belleville spring being inverted and nesting inside of the second Belleville spring, the drug container cannot be restored to the first position;
a housing to accommodate the drug container, wherein the housing comprises at least one flange;
a plunger, wherein the plunger can move axially within the housing, and is retained within the housing so the plunger cannot be removed; and
a needle, wherein pre-injection, the needle is in communication with the outlet port of the drug container.

2. The drug delivery device of claim 1, wherein the at least one bellow comprises a series of axially aligned bellows.

3. The drug delivery device of claim 1, wherein the drug container further comprises a distal end and a proximal end and a top, wherein the top is located at the proximal end of the drug container and is axially aligned with the at least one bellow.

4. The drug delivery device of claim 3, wherein the plunger has a proximal end and distal end, wherein the distal end of the plunger engages the proximal end of the drug container.

5. The drug delivery device of claim 4, wherein the distal end of the plunger is generally convex, and wherein the proximal end of the drug container is a mating proximal end that is generally concave.

6. The drug delivery device of claim 4, wherein the distal end of the plunger is generally concave, and wherein the proximal end of the drug container is a mating proximal end that is generally convex.

7. The drug delivery device of claim 1, wherein the drug container further comprises at least one priming bellow.

8. The drug delivery device of claim 1, wherein the at least one flange comprises two flanges.

9. The drug delivery device of claim 8, wherein the two flanges are partially enclosed.

10. The drug delivery device of claim 8, wherein the two flanges are fully enclosed.

11. The drug delivery device of claim 1, wherein the drug in the drug container is selected from the group consisting of oxytocin and carbetocin.

12. A drug delivery device comprising:
- a drug container comprising an outlet port, a top and at least one bellow axially aligned with the top, wherein each bellow of the at least one bellow comprises a first surface and a second surface, wherein the first surface is comprised of a first Belleville spring and the second surface is comprised of a second opposing Belleville spring, wherein the second Belleville spring has a higher spring rate than the first Belleville spring;
- a housing comprising at least one flange, wherein the housing extends between distal and proximal ends, wherein the proximal end is open to receive the drug container;
- a drug contained within the drug container;
- wherein the drug container can only move from a first position to a second position, wherein, in the first position, at least a portion of the drug container extends beyond the proximal end of the housing and wherein, in a second position, the first Belleville spring is inverted and nested inside of the second Belleville spring, and the top of the drug container is flush with the proximal end of the housing; wherein when the drug container is in the second position, the drug container has dispensed the drug and the first Belleville spring is inverted and nesting inside of the second Belleville spring such that the drug container cannot be restored to the first position, and the drug container cannot be refilled or reused; and
- a needle, wherein pre-injection, the needle is in communication with the outlet port of the drug container.

* * * * *